(12) United States Patent
Nancekievill et al.

(10) Patent No.: US 11,703,275 B2
(45) Date of Patent: Jul. 18, 2023

(54) SYSTEMS AND METHODS FOR REMOTELY MONITORING THE CRYOGENIC PROCESSING OF SAMPLES

(71) Applicant: Asymptote Ltd., Cambridge (GB)

(72) Inventors: Alexander Nancekievill, Cambridge (GB); Rupert Rutledge, Cambridge (GB)

(73) Assignee: Asymptote Ltd., Cambridge (GB)

( * ) Notice: Subject to any disclaimer, the term of this patent is extended or adjusted under 35 U.S.C. 154(b) by 737 days.

(21) Appl. No.: 16/689,175

(22) Filed: Nov. 20, 2019

(65) Prior Publication Data

US 2020/0103162 A1 Apr. 2, 2020

Related U.S. Application Data

(63) Continuation of application No. 16/463,705, filed as application No. PCT/GB2017/053532 on Nov. 24, 2017.

(30) Foreign Application Priority Data

Nov. 25, 2016 (GB) ..................... 1620017

(51) Int. Cl.
*B01L 7/02* (2006.01)
*F25D 29/00* (2006.01)
(Continued)

(52) U.S. Cl.
CPC ......... *F25D 29/001* (2013.01); *A01N 1/0257* (2013.01); *A01N 1/0273* (2013.01);
(Continued)

(58) Field of Classification Search
CPC . F25D 29/001; F25D 2600/06; A01N 1/0257; A01N 1/0273; A01N 1/0284
See application file for complete search history.

(56) References Cited

U.S. PATENT DOCUMENTS 6,646,564 B1  11/2003  Azieres et al.
8,681,419 B2  3/2014  Onaka
(Continued)

FOREIGN PATENT DOCUMENTS

CN  105371561 A  3/2016
CN  106148182 A  11/2016
(Continued)

OTHER PUBLICATIONS

Australia Government Examination Report 35530729 dated Oct. 26, 2021 (5 pages).
(Continued)

*Primary Examiner* — Filip Zec
(74) *Attorney, Agent, or Firm* — Eversheds Sutherland (US) LLP

(57) ABSTRACT

A remote system for monitoring and controlling one or more devices for use in the cryogenic processing of a sample is provided. A remote server capable of transmitting freezing profile data to one or more freezers, transmitting transportation profile data to one or more transportation devices, and transmitting thawing profile data to one or more thawing devices. The remote server is also capable of receiving detected data from the one or more freezers relating to the freezing of a sample in accordance with the freezing profile data, receiving detected data from the one or more transportation devices relating to the transportation of a sample in accordance with the transportation profile data, and receiving detected data from the one or more thawing machines relating to the thawing of a sample in accordance with the thawing profile data.

28 Claims, 18 Drawing Sheets

(51) Int. Cl.
  *G06F 9/451* (2018.01)
  *G06F 16/23* (2019.01)
  *A01N 1/02* (2006.01)
  *B01L 7/00* (2006.01)
  *H04L 67/125* (2022.01)

(52) U.S. Cl.
  CPC .............. *A01N 1/0284* (2013.01); *B01L 7/02* (2013.01); *B01L 7/50* (2013.01); *F25D 29/008* (2013.01); *G06F 9/451* (2018.02); *G06F 16/2379* (2019.01); *H04L 67/125* (2013.01); *B01L 2200/18* (2013.01); *B01L 2300/023* (2013.01); *B01L 2300/0663* (2013.01); *F25D 2600/06* (2013.01)

(56) References Cited

U.S. PATENT DOCUMENTS

| | | | |
|---|---|---|---|
| 8,794,012 | B2 | 8/2014 | Cheng |
| 9,872,250 | B2 | 1/2018 | Nicks et al. |
| 11,143,026 | B2 | 10/2021 | Sercel et al. |
| 2004/0053204 | A1 | 3/2004 | Morris et al. |
| 2004/0058432 | A1 | 3/2004 | Owen et al. |
| 2005/0241333 | A1* | 11/2005 | Hamilton ............... A01N 1/02 62/186 |
| 2011/0304466 | A1 | 12/2011 | Bair, III et al. |
| 2012/0102982 | A1* | 5/2012 | Zhou .................. A01N 1/0284 62/62 |
| 2014/0238048 | A1 | 8/2014 | Orndorff et al. |
| 2015/0192357 | A1* | 7/2015 | Thompson, Jr. ...... A01N 1/0252 62/62 |
| 2015/0204598 | A1 | 7/2015 | Affleck et al. |
| 2016/0047764 | A1 | 2/2016 | Cutting |
| 2018/0306651 | A1 | 10/2018 | Mitchell et al. |

FOREIGN PATENT DOCUMENTS

| | | |
|---|---|---|
| JP | H0861814 A | 2/1996 |
| JP | 2002366223 A | 12/2002 |
| JP | 2009236342 A | 10/2009 |
| JP | 2010161931 A | 7/2010 |
| WO | 91/01635 A2 | 2/1991 |
| WO | 2010/011766 A1 | 1/2010 |
| WO | 2010/083156 A1 | 7/2010 |
| WO | 2014/068508 A2 | 5/2014 |
| WO | 2015/038494 A1 | 3/2015 |
| WO | 2015/175819 A1 | 11/2015 |

OTHER PUBLICATIONS

Japanese Office Action for JP Application No. 2019-145529 dated Jul. 5, 2021 (8 pages with English translation).
JPO "Office Action" App. No. 2019-145530, dated Oct. 18, 2021, 5 pages.
Japanese Office Action for JP Application No. 2019-145531 dated Apr. 4, 2022 (7 pages).
PCT International Search Report and Written Opinion for PCT Application No. PCT/GB2017/053532 dated May 24, 2018 (19 pages).
Great Britain Search Report for GB Application No. 1620017.2 dated May 18, 2017 (3 pages).
Great Britain Search Report for GB Application No. 1620017.2 dated Jun. 30, 2017 (2 pages).
AU Examination Report No. 2 for App. No. 2019219749, Report dated Mar. 24, 2022, 5 pages.
European Office Action for EP Application No. 17807910.9 dated Aug. 17, 2022 (12 pages).
"What is ELLN2?" Cryogenic Control. 2018. pp. 1-6.
Japanese Office Action for JP Application No. 2019-528045 dated May 9, 2022 (7 pages).
Korean Office Action for KR Application No. 10-2019-7017795 dated Jul. 30, 2022 (5 pages with English Translation).
Korean Office Action for KR Application No. 10-2019-7029048 dated Jul. 30, 2022 (5 pages with English Translation).
Korean Office Action for KR Application No. 10-2019-7029049 dated Jul. 30, 2022 (5 pages with English Translation).
Korean Office Action for KR Application No. 10-2019-7029050 dated Jul. 30, 2022 (6 pages with English Translation).

* cited by examiner

SYSTEMS AND METHODS FOR REMOTELY MONITORING THE CRYOGENIC PROCESSING OF SAMPLES

CROSS REFERENCES TO RELATED APPLICATIONS

This application is a continuation of U.S. application Ser. No. 16/463,705 filed on May 23, 2019, which claims the priority benefit of PCT/GB2017/053532 filed on Nov. 24, 2017 which claims priority benefit of Great Britain Application No. 1620017.2 filed Nov. 25, 2016. The entire contents of which are hereby incorporated by reference herein.

BACKGROUND

The present techniques relate to systems and methods for remotely monitoring the cryogenic processing of samples. More particularly, the techniques relate to systems and methods for remotely monitoring the cryogenic freezing, the cryogenic storing, the cryogenic transportation and the cryogenic thawing of samples.

Cryogenic processing of a sample involves temperatures below −90° C. (−130° F.). The cryogenic freezing of a sample involves reducing the temperature of the sample to, or below, −90° C. The cryogenic thawing of a sample involves increasing the temperature of the sample from −90° C. or below. The cryogenic storing and the cryogenic transportation of a sample involves maintaining the temperature of the sample at, or below, −90° C. In most instances the cryogenic storing and the cryogenic transportation of a sample involves maintaining the temperature of the sample at the temperature at which it was cryogenically frozen.

Cryogenic processing can be utilised in many different fields, such as regenerative medicine, biobanks, atmospheric microphysics, conservation, assisted reproduction, transgenics, food processing, freeze drying. Cryogenic processing can be used for a variety of products, these include cells and tissues for clinical application for example in the fields of regenerative medicine, transplantation, transfusion and vaccination, where the requirement is to maintain cell viability and function on thawing, or tissue integrity and functionality. Cryogenic processing can be used can also be used with non cellular materials, for example with traditional vaccines and for acellular samples for biobanking.

SUMMARY OF THE INVENTION

The cryogenic processing described herein may be used for the transport of samples such as T cells and haematopoietic cells from patients to centres which manufacture immunotherapies or gene therapies, or biopsies from the operating theatre to biobanks for long term storage. The cryogenic processing described herein may also be used to transport manufactured cell products such as immunotherapies or gene therapies from the site of manufacturing to the patient.

In order to maintain, and confirm, the integrity of a sample at every point throughout its processing, from freezing to storage to transporting and to thawing, close monitoring of the sample is required.

According to a first aspect of the present techniques, there is provided a system for remotely monitoring cryogenic processing of a sample.

According to a second aspect of the present techniques, there is provided a method for remotely monitoring cryogenic processing of a sample.

According to a third aspect of the present techniques, there is provided a cryogenic freezer for freezing a sample in accordance with a sample freezing profile.

According to a fourth aspect of the present techniques, there is provided a cryogenic thawing machine for thawing a sample in accordance with a sample thawing profile.

According to a fifth aspect of the present techniques, there is provided a cryogenic transportation device for transporting a cryogenically frozen sample in accordance with a sample transportation profile.

According to a sixth aspect of the present techniques, there is provided a remote server for remotely monitoring cryogenic processing of a sample.

According to a seventh aspect of the present techniques, there is provided a computer program product comprising computer code for performing any of the methods described herein.

According to an eighth aspect of the present techniques, there is provided a system for remotely monitoring cryogenic processing of a sample.

According to a ninth aspect of the present techniques, there is provided a system for remotely monitoring cryogenic processing of a sample.

According to a tenth aspect of the present techniques, there is provided a system for remotely monitoring cryogenic processing of a sample.

According to an eleventh aspect of the present techniques, there is provided a system for remotely monitoring cryogenic processing of a sample.

According to a twelfth aspect of the present techniques, there is provided a system for remotely monitoring cryogenic processing of a sample.

According to a thirteenth aspect of the present techniques, there is provided a method for remotely monitoring cryogenic processing of a sample.

According to a fourteenth aspect of the present techniques, there is provided a method for remotely monitoring cryogenic processing of a sample.

Preferred features are set out in the appended dependent claims.

BRIEF DESCRIPTION OF THE DRAWINGS

Embodiments will now be described with reference to the accompanying Figures of which.

DETAILED DESCRIPTION

A remote system for monitoring and controlling one or more devices for use in the cryogenic processing (e.g. freezing, cooling and/or thawing) of a sample is provided. The remote system may use freezing profile data and/or thawing profile data for the cryogenic processing. A remote server is capable of transmitting freezing profile data to one or more freezers, transmitting storage profile data to one or more storage devices and/or transportation devices, and transmitting thawing profile data to one or more thawing devices. The remote server is also capable of receiving detected data from the one or more freezers relating to the freezing of a sample in accordance with the freezing profile data, receiving detected data from the one or more storage devices and/or transportation devices relating to the storage and/or transportation of a sample in accordance with the storage profile data, and receiving detected data from the one or more thawing machines relating to the thawing of a sample in accordance with the thawing profile data. The detected freezing data and/or the detected thawing data may be recorded/stored, and may be provided to a user/third party.

Figure 1:
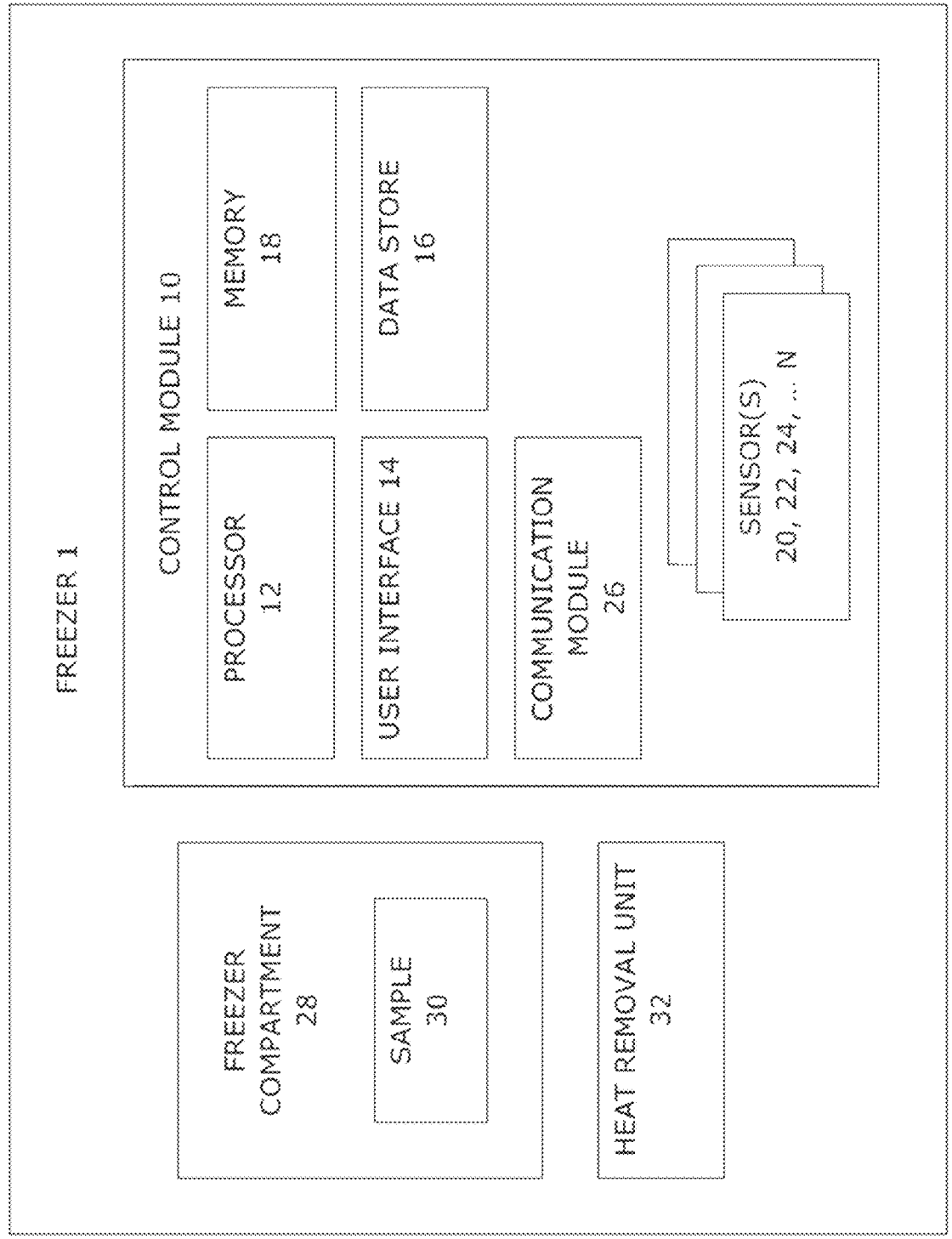
FIG. 1 schematically illustrates a cryogenic freezer.

In order to cryogenically freeze a sample, a cryogenic freezer, such as a freezer in the VIA FREEZE range by ASYMPTOTE can be used. FIG. 1 schematically illustrates a cryogenic freezer 1. As can be seen from FIG. 1, a cryogenic freezer 1 comprises a freezer compartment 28, within which a sample 30 to be frozen may be provided, coupled to a heat removal unit 32. The freezer 10 also comprises a control module 10 comprising at least one processor 12 coupled to at least one memory 18, at least one user interface 14, at least one communications interface 26, at least one data store 16, and at least one sensor 20, 22, 24 . . . n. The freezer 10 may also comprise other elements which are not illustrated.

The memory 18 may comprise program memory for storing computer program code to control the heat removal unit 32 in order to freeze a sample 30 as described herein, and working memory for storing data, programs, or instructions received or processed by the processor 12. The memory 18 and/or the data store 16 may comprise a volatile memory such as random access memory (RAM), for use as a temporary memory. Additionally or alternatively, the memory 18 and data store 16 may comprise non-volatile memory such as Flash, read only memory (ROM) or electrically erasable programmable ROM (EEPROM).

The processor 12 may comprise processing logic to process data (for example, data received from the sensors 20, 22, 24, . . . n, programs, instructions received from a user via the user interface 14 etc.) and generate output signals in response to the processing. The control module 10 may comprise any suitable circuitry or logic, and may, for example, comprise any one or more of the following: a field programmable gate array (FPGA), system on chip device, microprocessor device, microcontroller, and one or more integrated circuits. The control module 10 is coupled to the heat removal unit 32 in order to control the temperature in the freezer compartment 28.

The user interfaces 14 may be one or more of a computer screen, a touch screen, a keyboard, a mouse, speakers, a bar code scanner, a fingerprint scanner etc.

The communication module 26 may be conFigured to receive data or data signals from one or more external devices (such as a remote server as described herein). The communication module 26 may be a communication interface or unit. The communication module may be conFigured to receive data via a wired or wireless network, such as the internet. The communication module may also be conFigured to transmit data or data signals to one or more external devices (such as a remote server) via a wired or wireless network, such as the internet.

The data store 16 may be conFigured to store data from the sensors 20, 22, 24, . . . n. The data store 16 may be coupled to the at least one communication module 26 and the at least one processor 12.

The components of the control module 10 may be a combination of hardware and software components, all software components, or all hardware components.

Cryogenic freezers, such as illustrated in FIG. 1, cryogenically freeze a sample in accordance with a freezing profile. It is known that each sample variation requires its own freezing profile to be predetermined by a skilled scientist. A freezing profile is determined by a skilled scientist based on numerous factors such as the composition of the sample, the cell type or types used, the size (weight) of the sample, the nucleation temperature, the amount of cryoprotectant used, the container within which the sample is provided etc. Compounds with a protective impact during cryopreservation are referred to as cryoprotectants. In some embodiments, the cryoprotectant may be selected from dimethyl sulfoxide (DMSO), glycerol, glucose, propylene glycol, polyethylene glycol, sugars, alcohols, sugar alcohols, apoptosis inhibitors, ficoll, polyvinylpyrollidine, or a combination of two or more of these cryoprotectants, at concentrations ranging from 0 to 100%.

A freezing profile is specific to the factors upon which it is determined. For example, a freezing profile which is determined for 2 ml of sample A may be different from a freezing profile determined for 250 ml of sample A, or a freezing profile which is determined for 200 ml of sample A with 10% DMSO may be different from a freezing profile determined for 200 ml of sample A with 12% DMSO.

Figure 2:
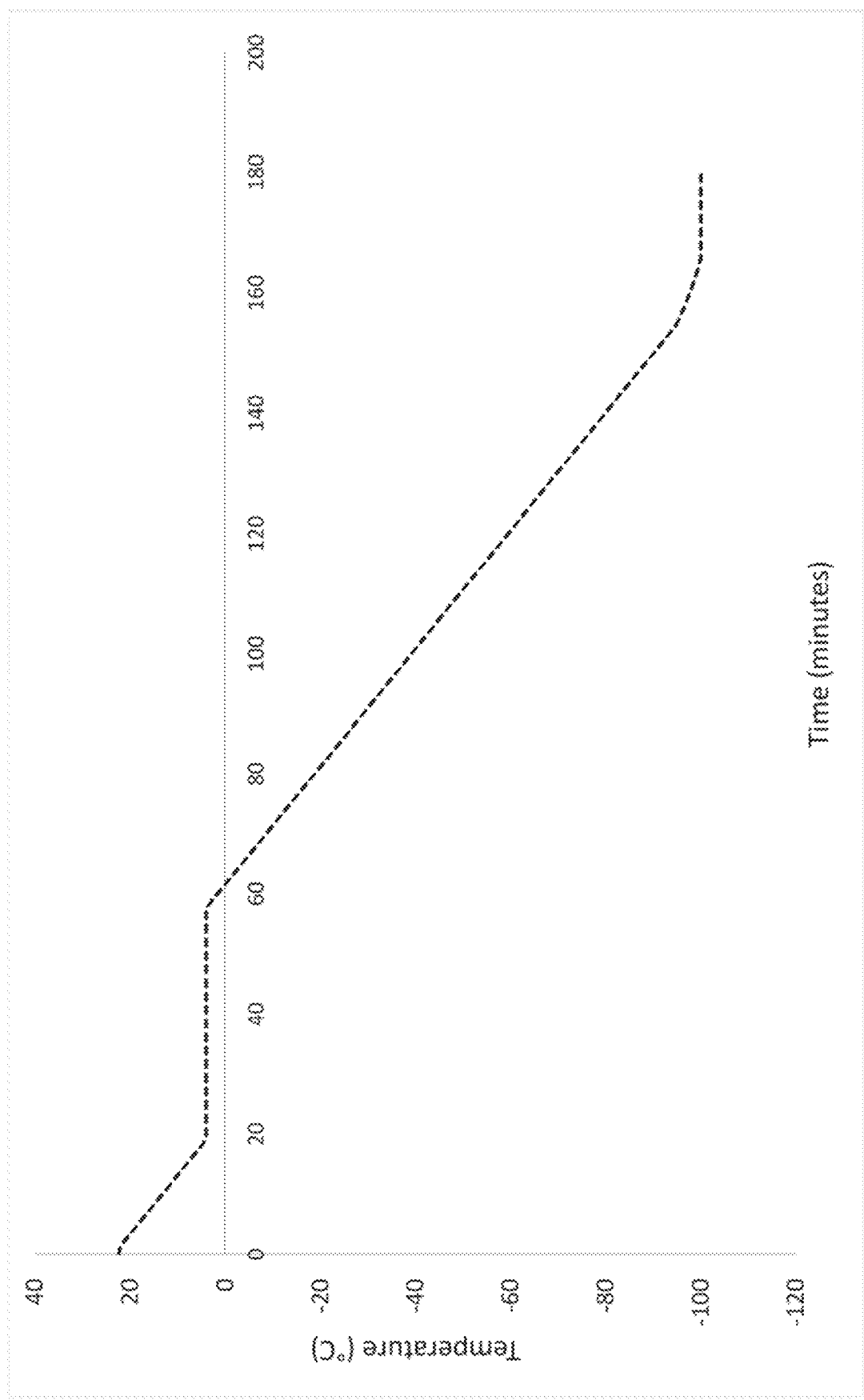
FIG. 2 illustrates a predetermined freezing profile.

FIG. 2 schematically illustrates an exemplary predetermined freezing profile for a sample (illustrated using a graph of temperature v's time). A freezing profile comprises a set of instructions, regardless of format, which are input into a freezer, and which define the rate of cooling of the sample during a freezing cycle. A freezing cycle begins at time t=0 minutes, when a sample is placed in a freezer. In most instances, a sample will be between room temperature and the sample's freezing point at the beginning of the freezing cycle. A freezing cycle ends when the sample has reached the desired temperature, which is defined in the freezing profile. For example, according to FIG. 2, the freezing cycle ends at time t=180 minutes.

A freezing profile may comprise different linear cooling rates (ramps), as well as constant-temperature holding times (dwells) etc. and may include linear and non-linear cooling protocols. As stated above, a freezing profile is predetermined for each sample variety. Whenever a sample is to be frozen, which has the same sample composition, sample size, amount of cryoprotectant, and container etc. as defined in a predetermined freezing profile, then that predetermined freezing profile is required to be programmed into the freezer. According to known systems, each predetermined freezing profile is provided to a human operator in paper form, normally as part of an instruction manual, and the human operator is required to enter the predetermined freezing profile via the user interface 14 at the freezer.

However, since the predetermined freezing profile is entered manually by a user, errors may occur, for example, typographical errors may be entered by the user of the system when copying the predetermined freezing profile from the paper version.

As stated above, the freezer 10 comprises at least one sensor 20, 22, 24 . . . n. One, or more, of the sensors 20, 22, 24 . . . n comprises a temperature sensor provided to monitor the temperature within the freezer compartment 28 during a freezing cycle. The temperature sensors detect the temperature at one or more different locations within the freezer compartment 28, such as at the plate within the freezer compartment 28. The temperature is detected during the freezing of a sample, in accordance with a predetermined freezing profile, and the data store 16 stores the detected temperatures together with the location of the sensors and/or a sensor ID and the time at which the temperature was sensed.

Figure 3:
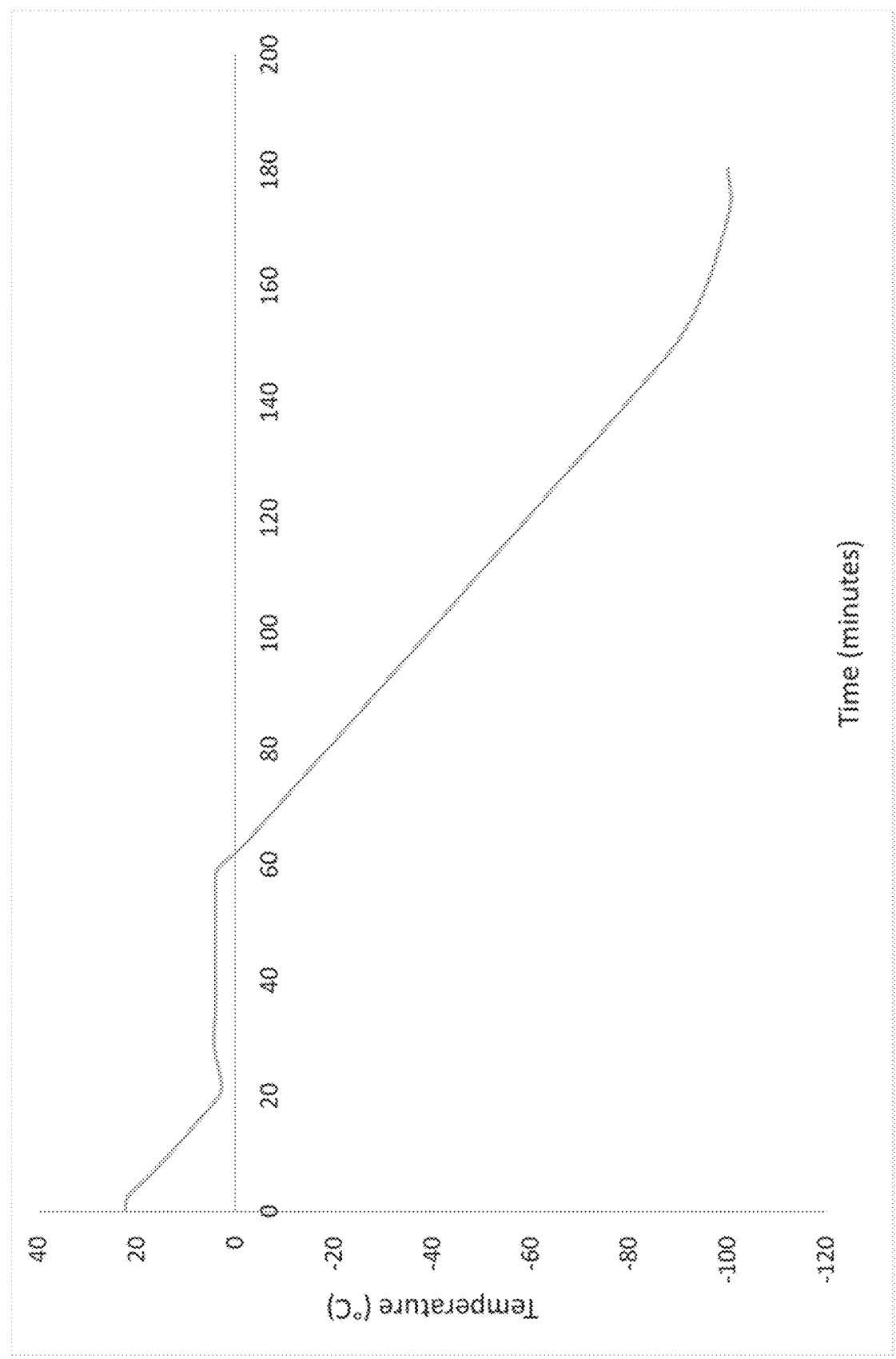
FIG. 3 illustrates a detected plate temperature during a freezing cycle.

FIG. 3 schematically illustrates a detected plate temperature v's time during the freezing of a sample in accordance with the predetermined freezing profile of FIG. 2.

In addition to detecting the temperature at different locations within the freezer compartment 28, one or more sensors 20, 22, 24 . . . n, can also be provided to detect the actual temperature of the sample during the freezing cycle. The sensors 20, 22, 24 . . . n, detect the actual temperature during the freezing of a sample, in accordance with a predetermined freezing profile, and the data store 16 stores the detected temperatures together with the location of the sensor and/or a sensor ID and the time at which the temperature was sensed.

Figure 4:
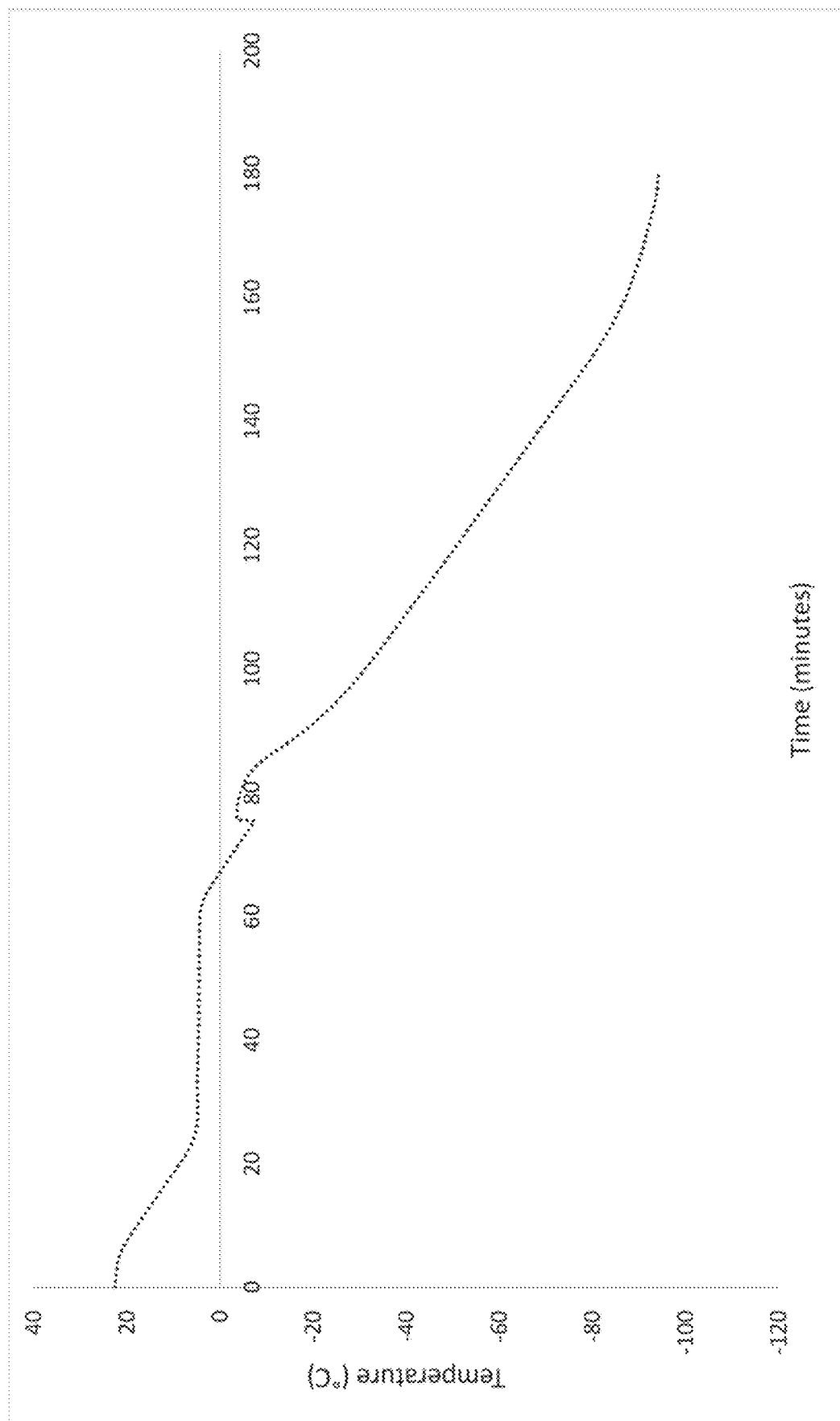
FIG. 4 illustrates a detected sample temperature during a freezing cycle.

FIG. 4 schematically illustrates a detected sample temperature v's time during the freezing of the sample in accordance with the predetermined freezing profile of FIG. 2.

Figure 5:
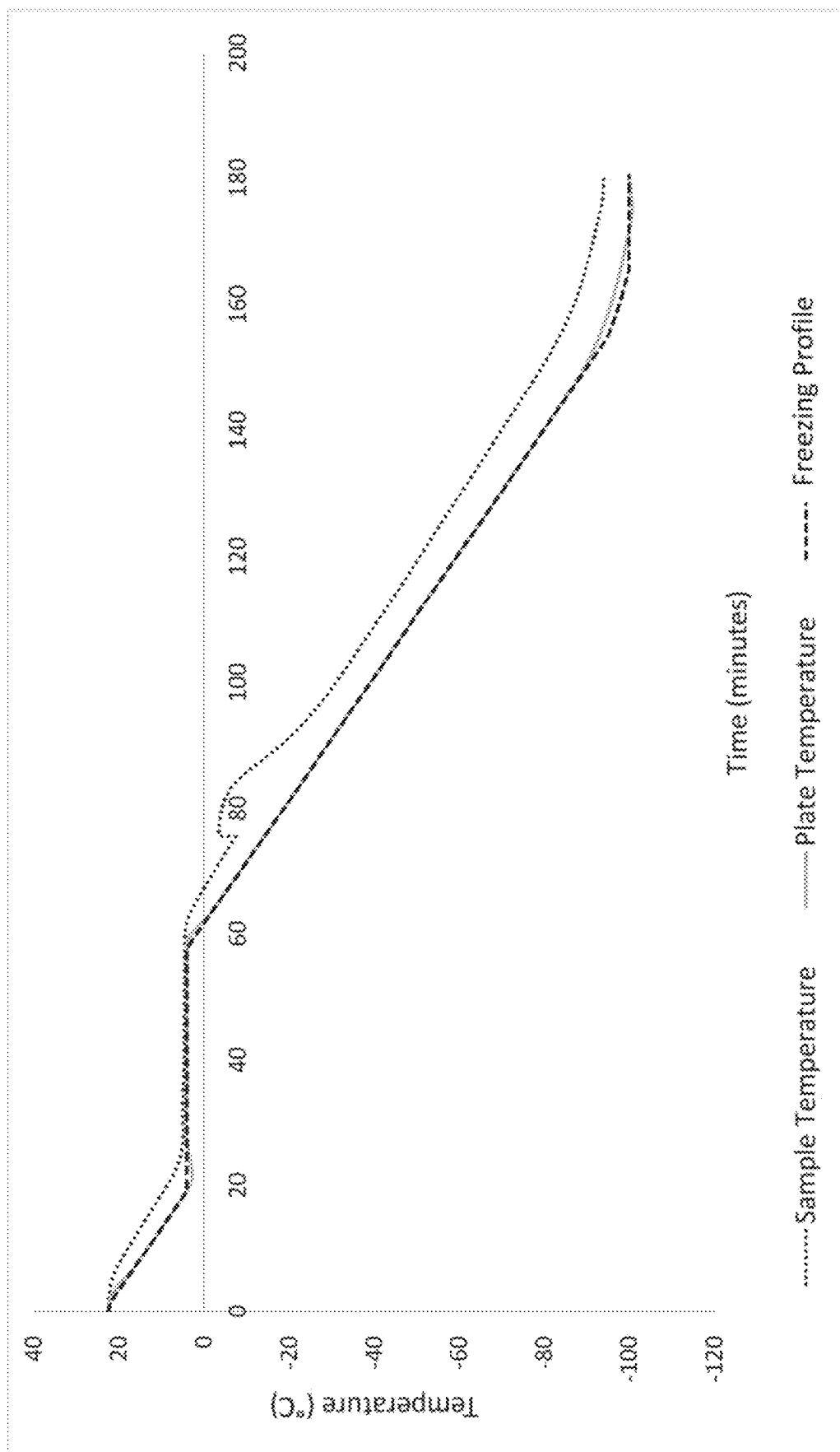
FIG. 5 illustrates the predetermined freezing profile of FIG. 2, the detected plate temperature of FIG. 3 and the detected sample temperature of FIG. 4.

FIG. 5 schematically illustrates the predetermined freezing profile of FIG. 2, the detected plate temperature of FIG. 3 and the detected sample temperature of FIG. 4. As is understood in the art, and as illustrated in FIG. 5, the actual detected freezing of a sample achieved by each freezer may vary from the predetermined freezing profile. Variations can occur as a result of numerous factors, such as the accuracy of the preparation of the sample. For example, a particular predetermined freezing profile may require 200 ml of sample A, mixed with 10% DMSO. However, one user 120, 121, 122, . . . , 12n may inadvertently add 195 ml of sample A mixed with 10.5% DMSO, or 202 ml of sample A mixed with 11% DMSO etc. Variations may also occur as a result of variations at the freezer, for example a freezers heat removal unit 32 may not be functioning as efficiently as possible.

In addition to detecting the actual temperatures during a freezing cycle, one or more sensors 20, 22, 24 . . . n may be provided to detect the external temperature at the freezer during a freezing cycle. In addition, one or more sensors may be provided to detect when the door of the freezer is opened, when the door of the freezer is closed, the time and date at which the door is opened/closed, and/or the duration of time the door was open.

According to one embodiment, the sensors 20, 22, 24 . . . n detect continuously during a freezing cycle. According to another embodiment, the sensors 20, 22, 24 . . . n detect periodically during a freezing cycle.

The sensor data detected by the sensors 20, 22, 24 . . . n relates to the freezing of a sample in accordance with a freezing profile. The sensor data detected by the sensors 20, 22, 24 . . . n may comprise one or more of: the temperature at one or more different locations within the freezer compartment 28 during a freezing cycle; the temperature of the sample during a freezing cycle; the external temperature at the freezer during a freezing cycle; freezer door data, such as when the door of the freezer is opened and/or closed during a freezing cycle and the duration of time the door was open for. For each detection, the time and date of the detection is also recorded together with an indication of the detecting sensor.

In addition to the sensor data detected by the sensors 20, 22, 24 . . . n, the control module 10 is also capable of detecting and storing other data which relates to the freezing of the sample in accordance with the freezing profile. The other data may comprise freezer data and/or sample data and/or user data etc. The control module 10 may store freezer data such as: a freezer identifier; freezer energy consumption (the energy consumed by the freezer during the freezing cycle and/or the energy consumed by different components of the freezer during the freezing cycle); freezer location (the actual location of the freezer and/or the freezers IP address); freezer alarm data (such as whether an alarm was activated at the freezer, for example, a door open alarm, and/or whether any action was taken in response to the alarm, for example, the door was closed). The control module 10 may store sample data such as: a sample identifier; sample composition data (such as information regarding the composition of the sample); sample size/weight data (such as information regarding the size/weight of the sample); sample container data (such as information regarding the sample container); the predetermined freezing profile; sample freeze date (such as the date the sample was frozen in accordance with the freezing profile); sample freeze time (such as the start time of the freezing cycle, the end time the freezing cycle, and/or the duration of the freezing cycle). The control module 10 may store user data such as: a user identifier; user observations, discussed in further detail below.

The sensor data detected by the sensors 20, 22, 24 . . . n, as well as the freezer data and/or sample data and/or user data, all of which relates to the freezing of a sample in accordance with a freezing profile, is of interest to a user. However, the user may not be at the location of the freezer, for example, because the user requires data from multiple freezers, or because the user is performing a clinical trial which requires data from multiple locations. Therefore, the communication module 26 may be used to transfer the data to a remote server.

Figure 6:
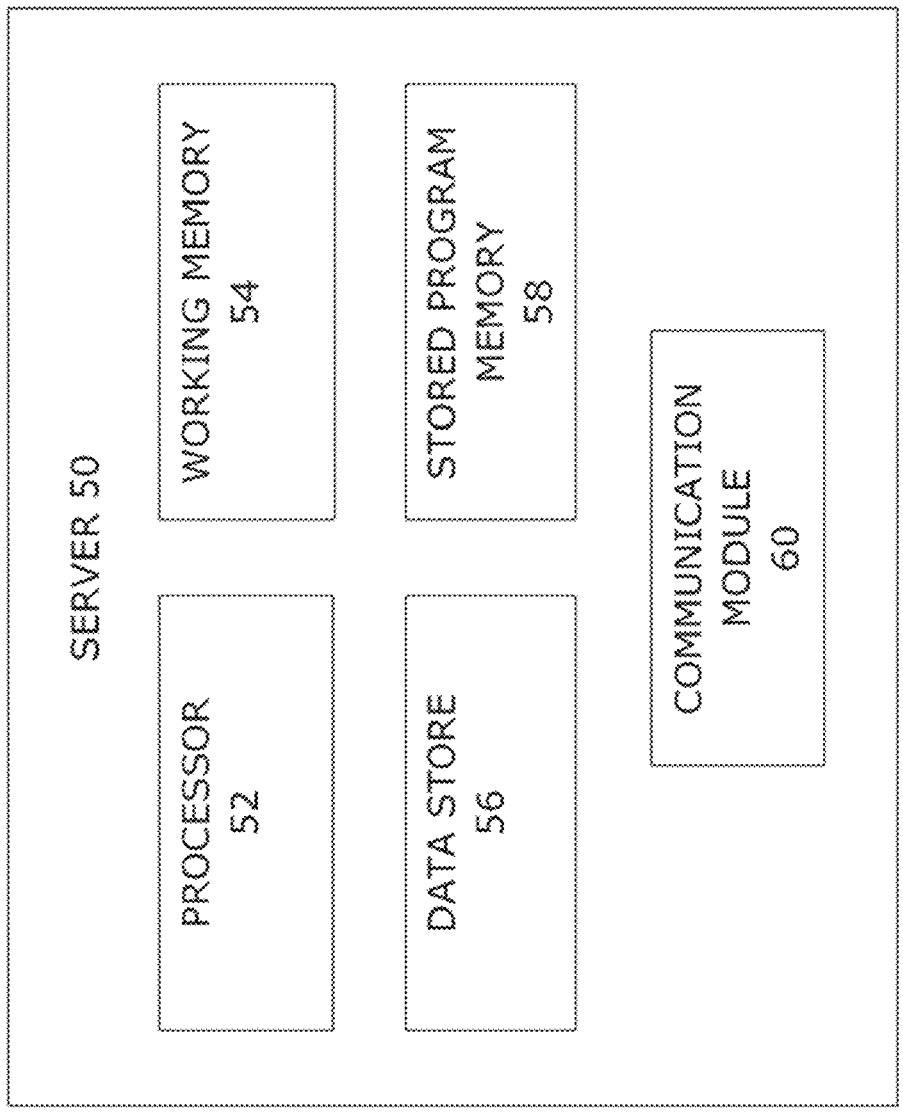
FIG. 6 schematically illustrates a remote server.

FIG. 6 illustrates schematically a remote server 50. The remote server 50 comprises at least one processor 52, at least one working memory 54, at least one stored program memory 58, at least one data store 56 and at least one communication module 60. The remote server 50 may also comprise other components which are not illustrated. The components of the remote server 50 may be a combination of hardware components and software components, may be all software components, or may be all hardware components, The remote server is communicatively coupled to at least one freezer. According to one embodiment, the communication module 60 is used to connect the remote server 50 to at least one cryogenic freezer over a network, such as the Internet. The connection may be wired or wireless. The at least one cryogenic freezer is then able to exchange data with the remote server 50. For example, the at least one cryogenic freezer is capable of transmitting data to the remote server 50, and the remote server 50 is capable of receiving the transmitted data from the at least one cryogenic freezer. In addition, the remote server 50 is capable of transmitting data to the at least one cryogenic freezer, and the at least one cryogenic freezer is capable of receiving the transmitted data from the remote server 50.

According to one embodiment, the data which is transferred between the freezer and the server is encrypted. For example, using a private/public key pair etc.

A user can access the remote server 50 from any computing device (such as a laptop computer, a tablet, a smart phone, a personal computer etc.) via a web browser. According to one embodiment, the user may be required to log into and have an account at the remote server. Following connection to the remote server 50, the user is able to access the data from the freezers. According to one embodiment, a data mining process may be applied to the data gathered at the remote server, in order to extract information and/or patterns from the data which would not have been possible without collating of the data.

Figure 7:
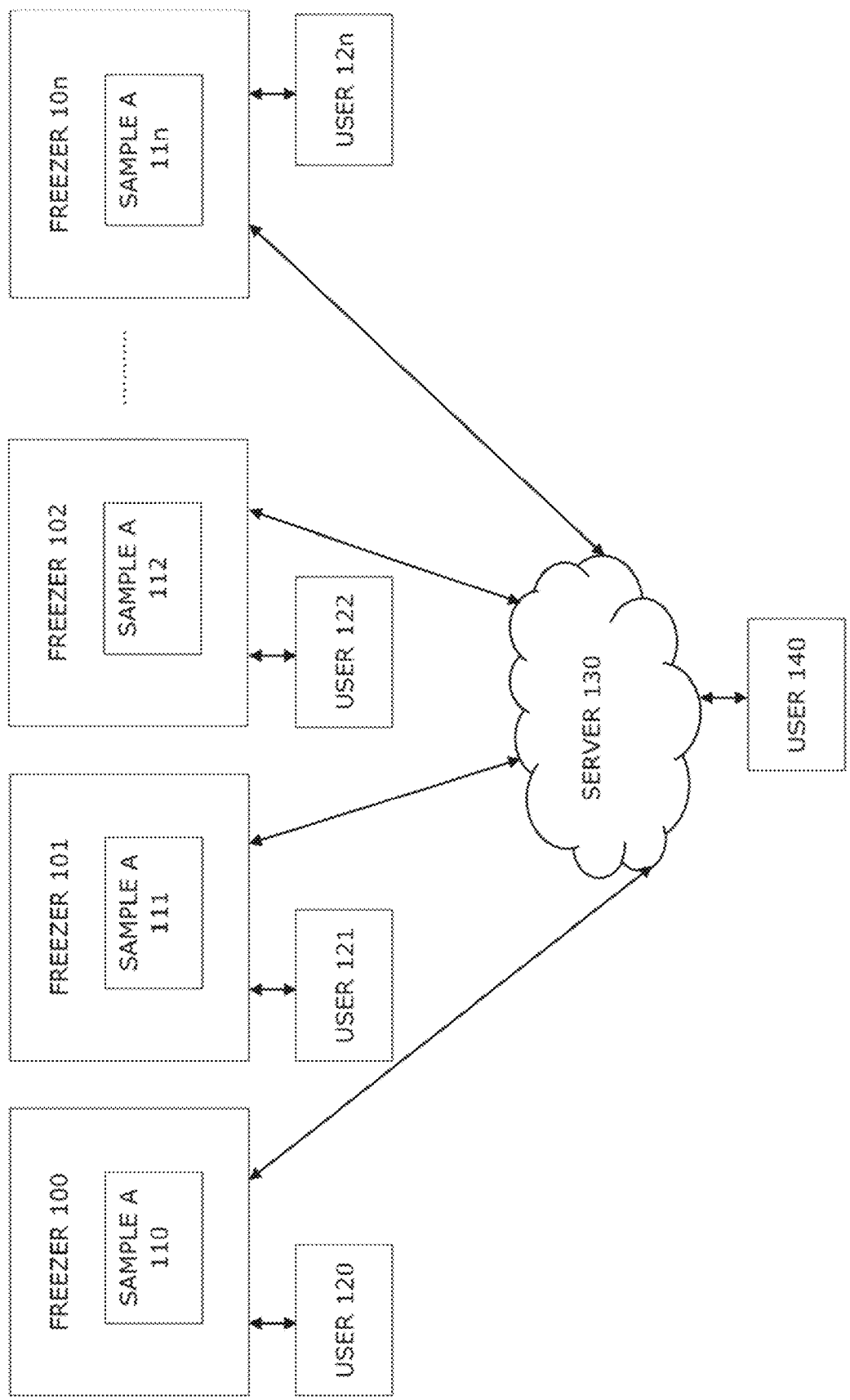
FIG. 7 schematically illustrates a system for monitoring one or more cryogenic freezers.

FIG. 7 illustrates schematically a system for monitoring one or more cryogenic freezers. A plurality of cryogenic freezers 100, 101, 102, . . . , 10n are illustrated in FIG. 7. For the avoidance of doubt, a plurality may be any number, including one. Each of the plurality of freezers 100, 101, 102, . . . , 10n may be provided at the same, or at different locations from the other freezers. Each freezer 100, 101, 102, . . . , 10n may be operated by a human operator (users 120, 121, 122, . . . , 12n). In addition, each freezer 100, 101, 102, . . . , 10n is communicatively coupled to a remote server 130. The remote server 130 is capable of receiving data from the freezers in order to monitor the freezers as well as transmitting data to the freezers.

As stated above, freezing profiles are predetermined by skilled scientists. The predetermined freezing profiles are then provided together with their associated criteria, such as the composition of the sample, the size of the sample, the amount and composition of cryoprotectant to be added to the sample, the type of container in which the sample is to be provided etc., to the remote server 130. According to one embodiment, the remote server 130 transmits the predetermined freezing profiles to the plurality of freezers 100, 101, 102, . . . , 10n. According to one embodiment, the predetermined freezing profiles may be transmitted to the plurality of freezers at substantially the same time. By transmitting the predetermined freezing profiles to the plurality of freezers, consistency can be increased, since the instances of human error when inputting the predetermined freezing profiles is reduced.

When a sample is required to be frozen at one of the plurality of freezers, the user 120, 121, 122, . . . , 12n at the freezer is only required to select the appropriate predetermined freezing profile, from a plurality of predetermined freezing profiles, via the user interface 14, such as a touch screen, at the freezer. The user 120, 121, 122, . . . , 12n at the freezer is not required to manually enter the predetermined freezing profile into the freezer. The user at the freezer may also be required to enter their user ID, via the user interface 14, before using the freezer. The user at the freezer may also be required to enter the sample ID, via the user interface 14, such as by using a touch screen, a bar code scanner when the sample ID is stored as a bar code, an imaging device when the sample ID is stored as a QR code etc.

Transmitting the predetermined freezing profiles to the plurality of freezers is also advantageous in that the user 140 at the remote server 130, can then guarantee that each freezer is using the same predetermined freezing profiles, when freezing the same sample. This is useful when identifying anomalies in data gathered from a plurality of freezer all running the same predetermined freezing profiles. Furthermore, when a predetermined freezing profile is updated by the skilled scientist, for example as a result of new data becoming available, an updated version of the predetermined freezing profile can be distributed to the plurality of freezers from the remote server, enhancing consistency across the network of freezers. According to one embodiment, the updated predetermined freezing profiles may be transmitted to the plurality of freezers at substantially the same time.

The predetermined freezing profiles may be provided to the plurality of freezers as a graph, such as illustrated in FIG. 2, or as a set of instructions. An exemplary set of instructions for the graph illustrated in FIG. 2 could be represented as:

| STEP | TIME (minutes) | TYPE | TEMPERATURE (° C.) |
|---|---|---|---|
| 1 | t = 0 | — | 22° C. |
| 2 | t = 0 to t = 20 | Ramp | from 22° C. to 4° C. |
| 3 | t = 20 to t = 58 | Dwell | at 4° C. |
| 4 | t = 58 to t = 154 | Ramp | from 4° C. to −92° C. |
| 5 | t = 154 to t = 165 | Ramp | from −92° C. to −100° C. |
| 6 | t = 165 to t = 180 | Dwell | at −100° C. |

When a predetermined freezing profile is selected at one of the plurality of freezers, the detected sensor data, freezer data, sample data and/or user data which relates to the freezing of a sample in accordance with the freezing profile is transmitted from the freezer to the remote server 130. The data may be transferred from the freezer to the remote server continuously, periodically or at the end of the freezing cycle, as required. Accordingly, the remote server may receive the data in near-real time. The remote server 130 stores the received data in the data store 56.

The detected freezing data, which relates to the freezing of a sample in accordance with a predetermined freezing profile, may be transferred from the freezer to the remote server 130 as a graph, such as illustrated in FIG. 4. Alternatively, the detected freezing data, which relates to the freezing of a sample in accordance with a predetermined freezing profile, may be transferred from the freezer to the remote server 130 as a plurality of data logs. In another alternative, the detected freezing data, which relates to the freezing of a sample in accordance with a predetermined freezing profile, may be transferred from the freezer to the remote server 130 as a combination of graph(s) and/or a plurality of data logs.

When the remote server 130 receives a plurality of detected data logs, the remote server may generate an actual freezing graph from the plurality of data logs representing the freezing of the sample, such as the graph illustrated in FIG. 4.

A user 140 can access the received freezing data, which relates to the freezing of a sample in accordance with a predetermined freezing profile, at the remote server 130. The server 130 can provide the user with the data from one or more freezers and/or one or more freezes. For example, a clinical trial may involve the freezing of a plurality of samples (of the same type) at a plurality of different freezers, all the freezers using the same freezing profile. The received data, regarding the plurality of freezes at a plurality of different freezers can then be presented to the user 140 in a user-friendly format. For example, the remote server 130 may generate a "freezing consistency report" from the received data. A "freezing consistency report" may provide the received freezing data, received from the plurality of freezers, on one graph, such that it easy for a user to look across a range of different freezers and/or freezes and to compare, for example, minimum, maximum and average freeze times. In addition, a tight grouping may indicate very consistent performance, whereas a wide spread may suggest something was not being well controlled. Furthermore, any anomalies in the received freezing data can be easily identified by a user. The "freezing consistency report" may also provide drop down filters so the user 140 can further tighten the analysis e.g. to a single freezer, a single user, a single freezing profile etc. The ability to store the data received from a plurality of different freezers regarding a plurality of different freezes is advantageous as anomalies can be identified quickly by a remote user. This is particularly beneficial for a user running a clinical trial, where previously a remote user would not have received the data, for maybe weeks after the freeze, and/or would not have received the same quantity or quality of data, since previously only the sensor freezing data would have been provided.

Figure 8:
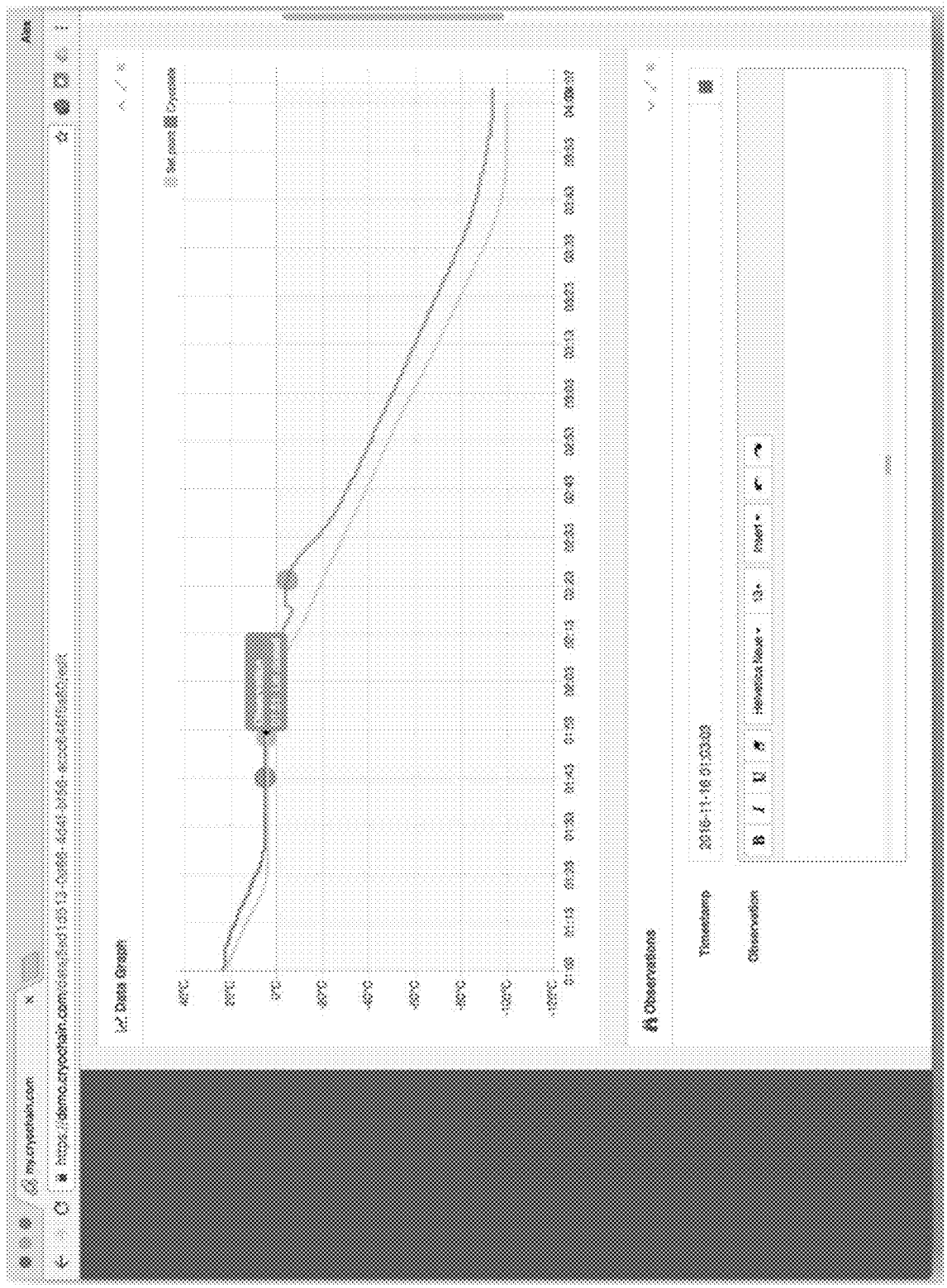
FIG. 8 illustrates a graph of the detected plate temperature of FIG. 3 and the detected sample temperature of FIG. 4 and annotated with "observations"

According to one embodiment, the remote server 130 may annotate the received freezing data with "observations". FIG. 8 illustrates an actual freezing graph which the remote sever has generated from the received data logs, and annotated with observations. The observations are generated by the remote server based on the data received from the freezer. For example, with reference to FIG. 8, the observation is "lid closed". The observation "lid closed" is determined from the received sensor data, for example, the door sensor data indicates that the door sensor detected that the lid was closed, at time 01:43. Therefore, the remote server adds an observation "lid closed" at time 01:43 to the received freezing data.

In addition, the operator of the freezer, user 120, 121, 122, ... , 12n, may create user observations and add notes, which are transferred from the freezer to the remote server 130. For example, when a biological sample is being frozen as part of a clinical trial, the user 120, 121, 122, ... , 12n may add an observation, such as the time that the sample was obtained from the patient, prior to the sample being frozen. These user observations are added at the freezer via the user interface 14 and transferred to the remote server 130 as user data together with the other data which relates to the freezing of a sample in accordance with a predetermined freezing profile.

The received sensor data, freezer data, sample data and/or user data, which relates to the freezing of the sample in accordance with the freezing profile, received at the remote server 130 can also be analysed in order to perform checks on the freezing process. For example, a predetermined freezing profile may require approximately 500 joules of energy to complete the freeze. When five of the freezers transfer data indicating that they completed the freezing cycle in accordance with the predetermined freezing profile using approximately 500 joules of energy, but one of the freezers transfers data indicating that it completed the freezing cycle in accordance with the predetermined freezing profile using 800 joules of energy, then it is possible to determine that an unknown event has occurred at that freezer, and further investigation is required. Previously it would not have been possible to compare such data and therefore, it would not have been possible to identify that an unknown event has occurred at the freezer which required further investigation.

According to one embodiment, the remote server may provide a suggestion as to what the event might be. For example, if additional power was required to freeze the sample, then the server may suggest that the sample was of a size greater than that indicated for the selected predetermined freezing profile. According to one embodiment, the server may provide alerts to a user. For example, most freezers comprise an alarm to indicate to a user in the proximity of the freezer when a door has been left open. However, the remote server may also provide alerts direct to a user, such as to a user's mobile device, when an event has occurred at the freezer. The alerts may be visual and/or audible alerts.

Figure 9:
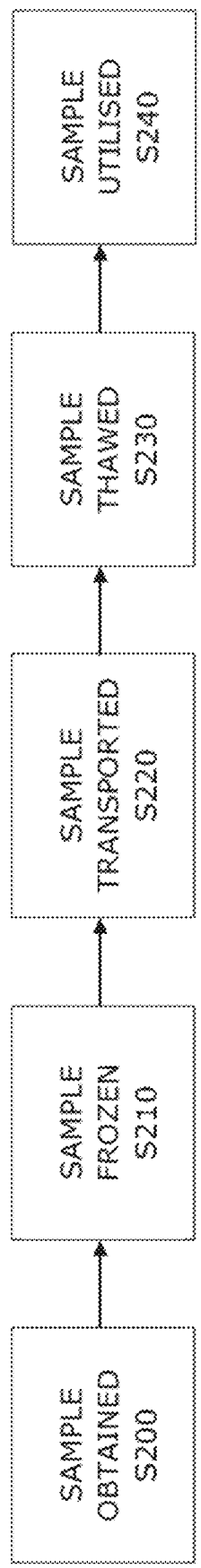
FIG. 9 schematically illustrates an overview of the processing of a biological sample.

The cryogenic freezing of a sample is normally only one stage in the processing of a biological sample. FIG. 9 illustrates schematically a simple overview of the processing of a biological sample. As illustrated in FIG. 9, the sample is obtained at step S200. The sample is then frozen at a controlled-rate, in accordance with a predetermined freezing profile, at step S210, such as described above. Following freezing, the sample may be required to be stored and/or transported to another location at step S220 prior to controlled thawing at step S230, and utilisation at step S240. In between freezing and thawing, the sample is required to be cryogenically stored whilst being transported, if required to another location. It is important to the integrity of the sample that the sample be kept in predetermined conditions at all of these stages.

Data recorded at each of these stages may be transferred to the remote server 130, either continuously, periodically or at the end of each stage in the process, as required.

Figure 10:
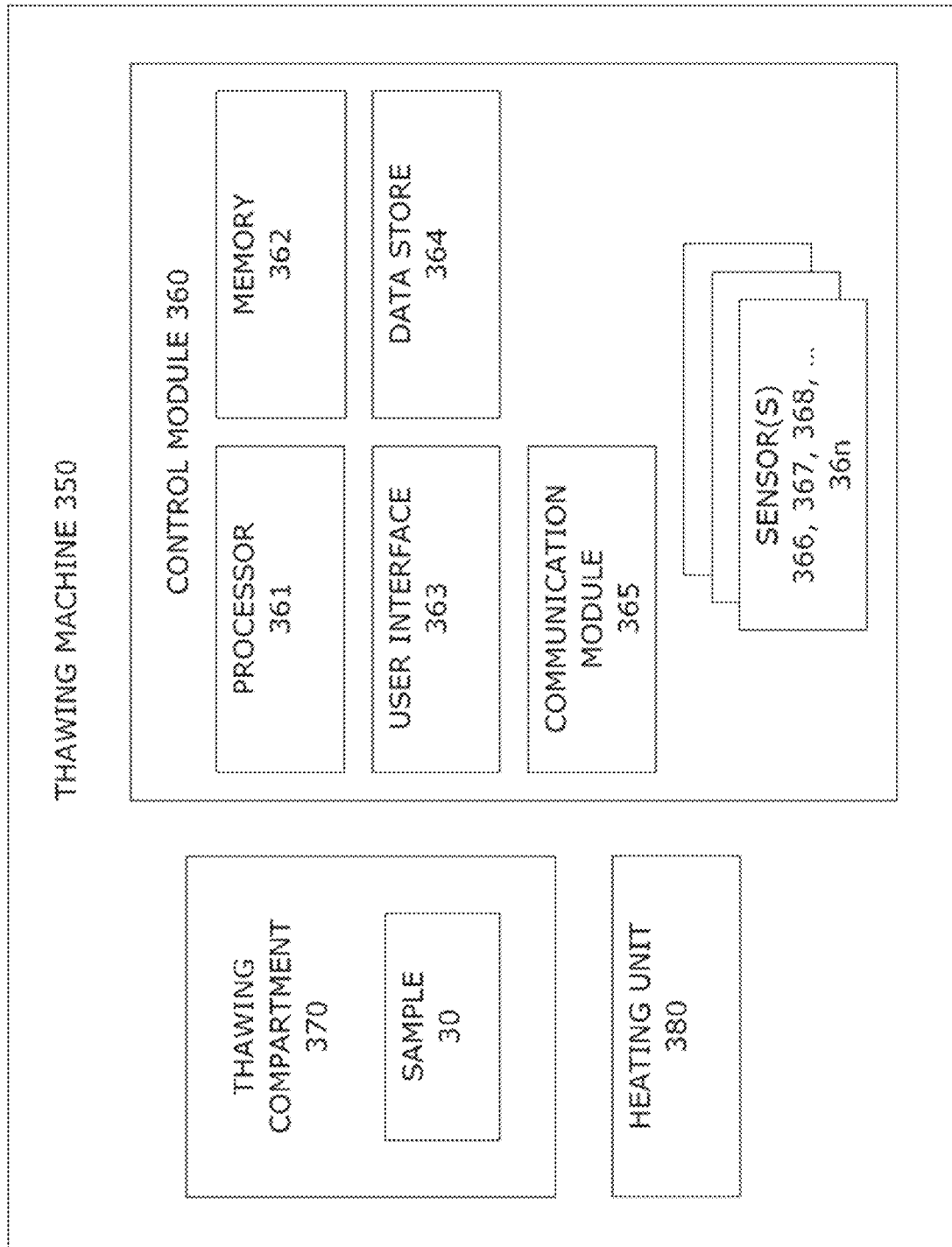
FIG. 10 schematically illustrates a thawing machine.

A thawing machine, for example, a VIA THAW machine by ASYMPTOTE may be used to provide controlled thawing of a sample. FIG. 10 schematically illustrates a thawing machine 350. As can be seen from FIG. 10, a thawing machine 350 comprises a thawing compartment 370, for example, a water bath, within which a sample 30 to be thawed may be provided, coupled to a heating unit 380. The thawing machine 350 also comprises a control module 360 comprising at least one processor 361 coupled to at least one memory 363, at least one user interface 363, at least one communications interface 365, at least one data store 364, and at least one sensor 366, 367, 368, ... 36n. The thawing machine 350 may also comprises other elements which are not illustrated.

The memory 363 may comprise program memory for storing computer program code to control the heating unit 380 in order to thaw a sample 30 provided in the thawing compartment 370, as described herein, and working memory for storing data, programs, or instructions received or processed by the processor 361. The memory 363 and/or the data store 364 may comprise a volatile memory such as random access memory (RAM), for use as temporary memory. Additionally or alternatively, the memory 363 and data store 364 may comprise non-volatile memory such as Flash, read only memory (ROM) or electrically erasable programmable ROM (EEPROM).

The processor 361 may comprise processing logic to process data (for example, data received from the sensors 366, 367, 368, . . . 36n, programs, instructions received from a user via the user interface 363 etc.) and generate output signals in response to the processing. The control module 360 may comprise any suitable circuitry or logic, and may, for example, comprise any one or more of the following: a field programmable gate array (FPGA), system on chip device, microprocessor device, microcontroller, and one or more integrated circuits. The control module 360 is coupled to the heating unit 380 in order to control the temperature in the thawing compartment 370.

The user interfaces 363 may be one or more of a computer screen, a touch screen, a keyboard, a mouse, speakers, a bar code scanner, a fingerprint scanner etc.

The communication module 365 may be conFigured to receive data or data signals from one or more external devices (such as a remote server as described herein). The communication module 365 may be a communication interface or unit. The communication module 365 may be conFigured to receive data via a wired or wireless network, such as the internet. The communication module 365 may also be conFigured to transmit data or data signals to one or more external devices (such as a remote server) via a wired or wireless network, such as the internet.

The data store 364 may be conFigured to store data from the sensors 366, 367, 368, . . . 36n. The data store 364 may be coupled to the at least one communication module 365 and the at least one processor 361.

The components of the control module 360 may be a combination of hardware and software components, all software components, or all hardware components.

Cryogenic thawing machines, such as illustrated in FIG. 10, thaw a sample in accordance with a thawing profile. Each sample requires its own thawing profile to be determined by a skilled scientist. As with the freezing profile, each thawing profile is determined based on numerous factors such as the composition of the sample, the size (weight) of the sample, the amount of cryoprotectant added to the sample prior to freezing, the container within which the sample is provided etc.

Figure 11:
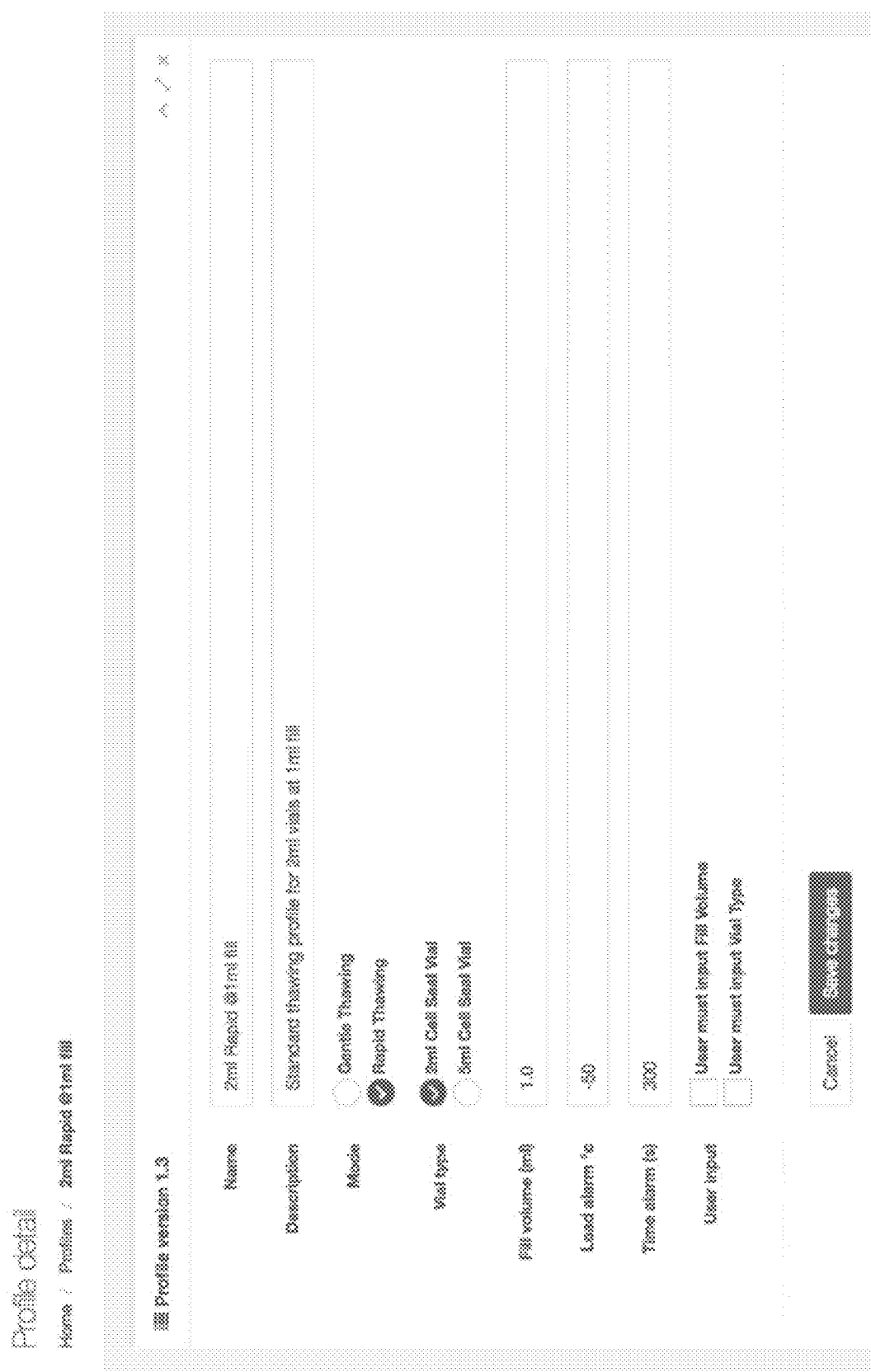
FIG. 11 illustrates a thawing profile.

A thawing profile is normally simpler than a freezing profile and specifies, for example: a heating unit temperature; container type; container size (ml); what temperature will trigger a "too warm" alert when a sample is loaded into the thawing machine for thawing; what time will trigger a "too long" alert when a sample has taken too long to thaw. According to one embodiment, a thawing profile is defined as a list of instructions. FIG. 11 illustrates an exemplary thawing profile.

Figure 12:
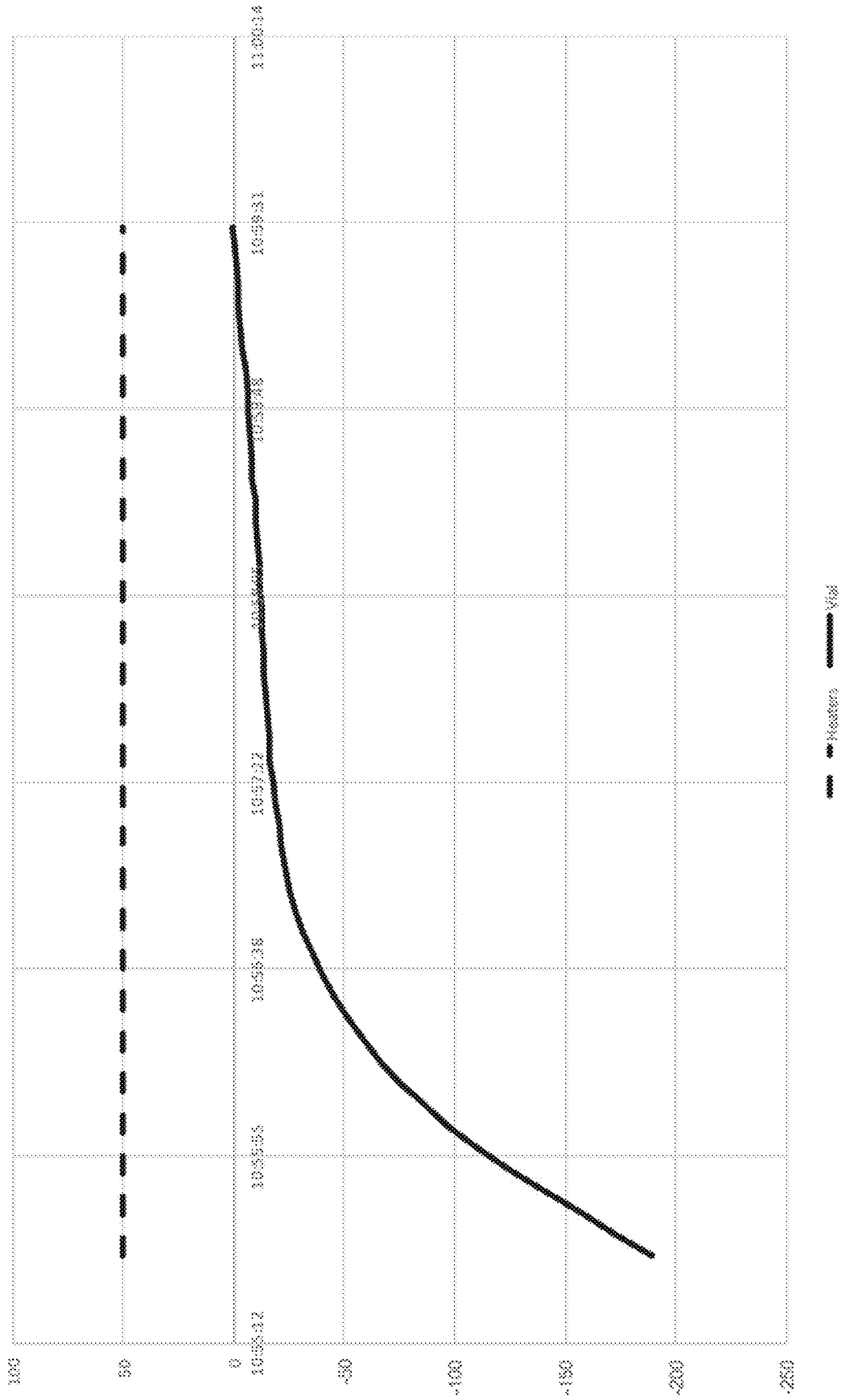
FIG. 12 illustrates a detected sample temperature during a thawing cycle.

FIG. 12 illustrates an exemplary detected thawing sample temperature (continuous line) together with the heater temperature (dotted line).

A thawing profile comprises a set of instructions, regardless of format, which are input into a thawing machine, and which defines the rate at which a sample heats up during a thawing cycle. A thawing cycle begins at time t=0 minutes, when a sample is placed in a thawing machine. A thawing cycle ends when the sample has reached the desired temperature, which in most instances is just above the sample's melting point.

As stated above, the thawing machine 350 comprises at least one sensor 366, 367, 368, . . . 36n. One, or more, of the sensors 366, 367, 368, . . . 36n comprises a temperature sensor provided to monitor the temperature within the thawing compartment 370 during a thawing cycle. The temperature sensors also detect the temperature at the heating unit 380 during a thawing cycle. The detected temperatures are stored in the data store 364 together with the location of the sensor and/or a sensor ID and the time at which the temperature was sensed.

In addition to detecting the temperatures within the thawing machine during a thawing cycle, one or more sensors 366, 367, 368, . . . 36n may be provided to detect the external temperature at the thawing machine during a thawing cycle. In addition, one or more sensors may be provided to detect when the door of the thawing machine is opened, when the door of the thawing machine is closed, the time and date at which the door is opened/closed, and/or the duration of time the door was open.

According to one embodiment, the sensors 366, 367, 368, . . . 36n detect continuously during a thawing cycle. According to another embodiment, the sensors 366, 367, 368, . . . 36n detect periodically during a thawing cycle.

The sensor data detected by the sensors 366, 367, 368, . . . 36n relates to the thawing of a sample in accordance with a thawing profile. The sensor data detected by the sensors 366, 367, 368, . . . 36n may comprise one or more of: the temperature, at one or more locations within the thawing compartment during a thawing cycle; the temperature at the heating unit during a thawing cycle; the external temperature at the thawing machine during a thawing cycle; thawing machine door data, such as when the door of the thawing machine is opened and/or closed during a thawing cycle. For each detection, the time and date of the detection is also recorded together with an indication of the detecting sensor.

In addition to the sensor data detected by the sensors 366, 367, 368, . . . 36n, the control module 360 is also capable of detecting and storing other data which relates to the thawing of the sample in accordance with the thawing profile. The other data may comprise thawing machine data and/or sample data and/or user data etc. The control module 360 may store thawing machine data such as: a thawing machine identifier; thawing machine energy consumption (for example, the energy consumed by the thawing machine during a thawing cycle and/or the energy consumed by different components of the thawing machine during a thawing cycle); thawing machine location (for example, the actual location of the thawing machine and/or the thawing machines IP address); thawing machine alarm data, such as whether an alarm was activated at the thawing machine (for example, a sample too warm alarm) and/or whether any action was taken in response to the alarm. The control module 360 may store sample data such as: a sample identifier; sample composition data (such as information regarding the composition of the sample); sample size/weight data (such as information regarding the size/weight of the sample); sample container data (such as information regarding the sample container; the predetermined thawing profile; sample thaw date (such as the date the sample was thawed in accordance with the thawing profile); sample thaw time (such as the start time of the thawing cycle, the end time the thawing cycle and/or the duration of the thawing cycle). The control module 10 may store user data such as: a user identifier; user observations, discussed in further detail below.

The sensor data detected by the sensors 366, 367, 368, . . . 36n, as well as the thawing machine data and/or sample data and/or user data, all of which relates to the thawing of a sample in accordance with a thawing profile, is of interest to a user. However, the user may not be at the location of the thawing machine, for example, because the user requires data from multiple thawing machines, or because the user is performing a clinical trial which requires data from multiple locations. Therefore, the communication module 365 may be used to transfer the detected data from the thawing machine to a remote server 50, such as described above and illustrated in FIG. 6.

Figure 13:
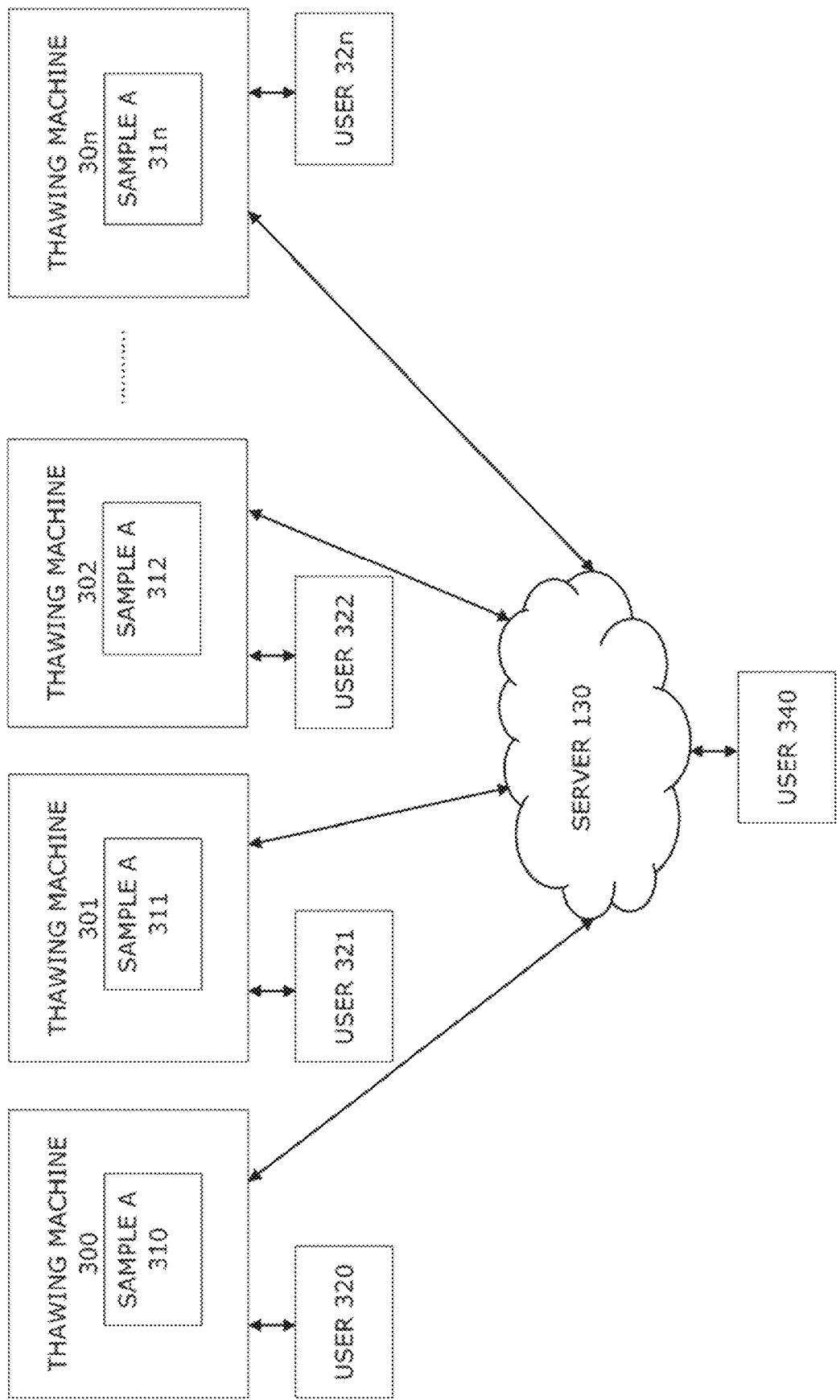
FIG. 13 schematically illustrates a system for monitoring one or more thawing machines.

FIG. 13 illustrates schematically a system for monitoring one or more thawing machines. A plurality of thawing machines 300, 301, 302, ..., 30n are illustrated in FIG. 13. Each of the plurality of thawing machines 300, 301, 302, ..., 30n may be provided at the same, or at different locations from the other thawing machines. In addition, each of the plurality of thawing machines 300, 301, 302, ..., 30n may be provided at the same location as a freezer, or at different location from a freezer. Each thawing machine 300, 301, 302, ..., 30n may be operated by a human operator (users 320, 321, 322, ..., 32n). In addition, each thawing machine 300, 301, 302, ..., 30n is communicatively coupled to a remote server 130.

The remote server 130 is communicatively coupled to at least one thawing machine. According to one embodiment, the communication module 60 is used to connect the remote server to at least one thawing machine over a network, such as the Internet. The connection may be wired or wireless. The plurality of thawing machines 300, 301, 302, ..., 30n are able to exchange data with the remote server 130. For example, the plurality of thawing machines 300, 301, 302, ..., 30n are capable of transmitting data to the remote server 130, and the remote server 130 is capable of receiving the transmitted data from the plurality of thawing machines 300, 301, 302, ..., 30n. In addition, the remote server 130 is capable of transmitting data to the plurality of thawing machines 300, 301, 302, ..., 30n, and the plurality of thawing machines 300, 301, 302, ..., 30n are capable of receiving the transmitted data from the remote server 130.

According to one embodiment, the data which is transferred between the thawing machine and the server is encrypted, for example, using a private/public key pair etc.

As stated above, the thawing profiles are predetermined by skilled scientists. The predetermined thawing profiles are provided together with their associated criteria, such as the composition of the sample, the size of the sample, the amount of cryoprotectant to be added to the sample, the type of container in which the sample is to be provided etc. to the remote server 130. According to one embodiment, the remote server 130 transmits the predetermined thawing profiles to the plurality of thawing machines 300, 301, 302, ..., 30n. The predetermined thawing profiles may be transmitted to the plurality of thawing machines 300, 301, 302, ..., 30n at substantially the same time. When a predetermined thawing profile is updated by a skilled scientist, an updated version of the predetermined thawing profile may be distributed to the plurality of thawing machines from the remote server. The updated predetermined thawing profiles may be transmitted to the plurality of thawing machines at substantially the same time.

When a sample is required to be thawed at one of the plurality of thawing machines, the user 320, 321, 322, ..., 32n at the thawing machine is only required to select the appropriate predetermined thawing profile, from a plurality of predetermined thawing profiles, via the user interface 363, such as a touch screen, at the thawing machine. The user 320, 321, 322, ..., 32n at the thawing machine is not required to manually enter the predetermined thawing profile into the thawing machine. The user 320, 321, 322, ..., 32n at the thawing machine may also be required to enter their user ID, via the user interface 363, before using the thawing machine. The user at the thawing machine may also be required to enter the sample ID, via the user interface 363, such as by using a touch screen, a bar code scanner when the sample ID is stored as a bar code, an imaging device when the sample ID is stored as a QR code etc., before using the thawing machine.

As is understood in the art, an actual thawing temperature achieved by each thawing machine may vary from the predetermined thawing profile. Variations can occur as a result of numerous factors, such as the accuracy of the preparation of the sample. For example, a predetermined thawing profile may specify that thawing begins at the temperature at which the sample is frozen and/or stored (as appropriate). However, the actual sample will start thawing the moment it is removed from its storage unit, therefore, the actual temperature of the sample when it enters the thawing machine may be different from that defined in the thawing profile. This is particularly evident when the transfer of the sample from the storage device to the thawing machine is not instantaneous. For example, when a sample is being kept at −196° C., it will start thawing very quickly when removed from its storage environment to room temperature prior to been provided in the thawing machine. Such variations from the specified criteria of the predetermined thawing profile may result in detected thawing data, such as the sample temperature, which is different from the predetermined thawing profile.

When a predetermined thawing profile is selected at one of the plurality of thawing machines, and a sample is thawed in accordance with the selected predetermined thawing profile, the detected sensor data, thawing machine data, sample data and/or user data, which relates to the thawing of the sample in accordance with the predetermined thawing profile, is transmitted from the thawing machine to the remote server 130. The data may be transferred from the thawing machine to the remote server continuously, periodically or at the end of the thawing cycle, as required. Accordingly, the remote server may receive the data in near-real time. The remote server 130 stores the received data in the data store 56.

The detected thawing data, which relates to the thawing of a sample in accordance with the predetermined thawing profile, may be transferred from the thawing machine to the remote server 130 as a graph, such as illustrated in FIG. 12. Alternatively, the detected thawing data, which relates to the thawing of a sample in accordance with the predetermined thawing profile, may be transferred from the thawing machine to the remote server 130 as a plurality of data logs of what actually happened whilst the sample was being thawed. In another alternative, the detected thawing data, which relates to the thawing of a sample in accordance with the predetermined thawing profile, may be transferred from the thawing machine to the remote server 130 as a combination of graph(s) and/or a plurality of data logs.

When the remote server 130 receives a plurality of data logs, the remote server may generate an actual thawing graph from the plurality of data logs, representing the thawing of the sample, such as the graph illustrated in FIG. 12.

A user 140 can then access the received data, which relates to the thawing of a sample in accordance with the predetermined thawing profile, at the remote server 130. The server 130 can provide the user with the data from one or more thawing machines and/or one or more thaws. For example, a clinical trial may involve the thawing of a plurality of samples (of the same type) at a plurality of different thawing machines, all of the thawing machines using the same predetermined thawing profile. The data regarding the plurality of thaws at the plurality of different thawing machines can then be presented to the user 140 in a user-friendly format. For example, the remote server 130 may generate a "thawing consistency report" from the received data. A "thawing consistency report" may provide the received thawing data, received from the plurality of thawing machines, on one graph, such that it easy for a user to look across a range of different thawing machines and/or thaws and to compare, for example, minimum, maximum and average thaw times. In addition, a tight grouping may indicate very consistent performance, whereas a wide spread may suggest something was not being well controlled. Furthermore, any anomalies in the received thawing data may be easily identified by a user. The "thawing consistency report" may also provide drop down filters so the user can further tighten the analysis e.g. to a single thawing machine, a single user, a single thawing profile etc. The ability to store the data received from a plurality of different thawing machines regarding a plurality of different thaws is advantageous as anomalies can be identified quickly by a remote user. This is particularly beneficial for a user running a clinical trial, where previously a remote user would not have received the data, for maybe weeks after the thaw, and/or would not have received the same quantity of data, since previously only the detected temperature data may be provided.

Figure 14:
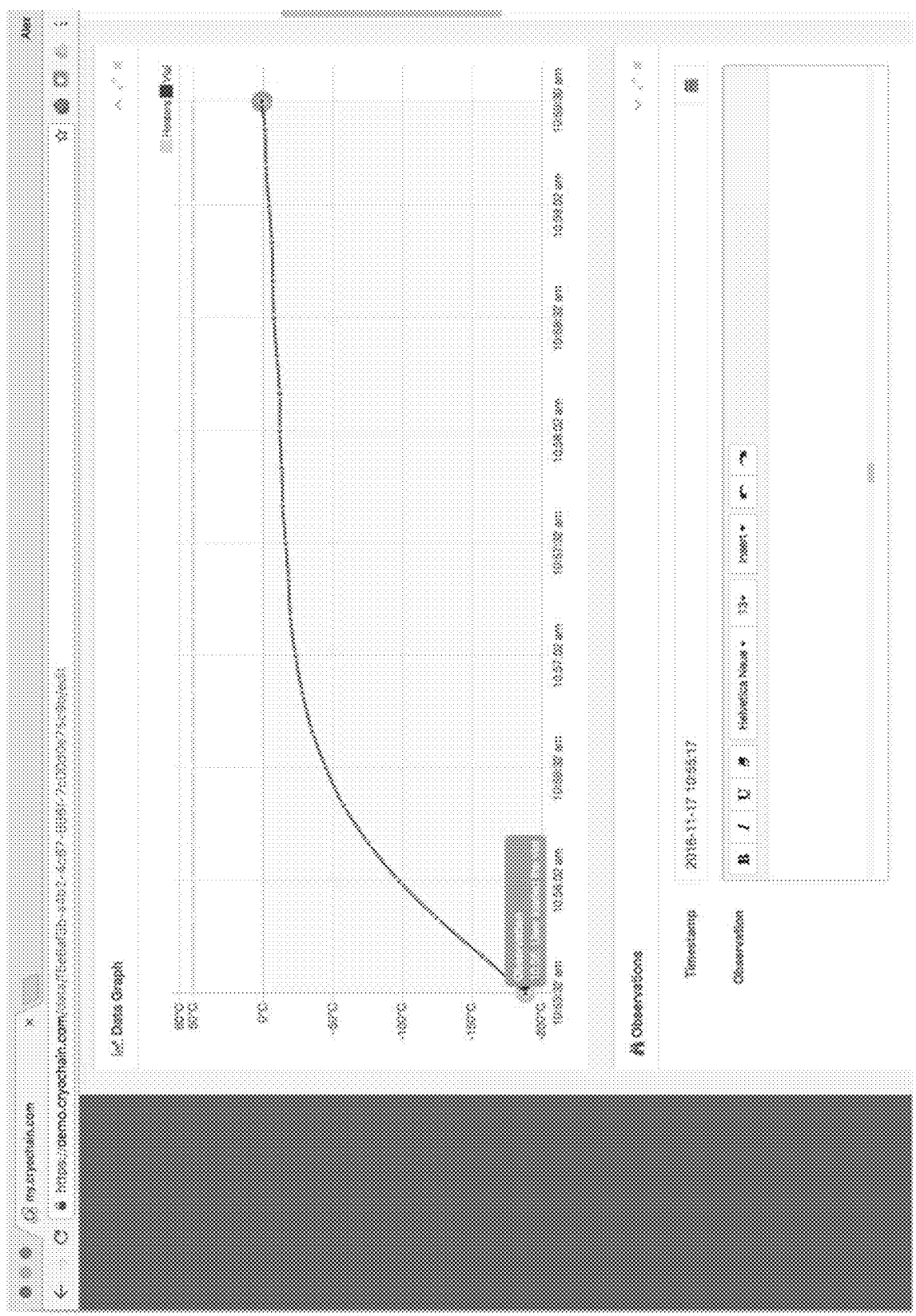
FIG. 14 illustrates the detected sample temperature of FIG. 12 as transferred to the server of FIG. 6 and annotated with "observations"

According to one embodiment, the remote server 130 may annotate the received thawing data with "observations". FIG. 14 illustrates a detected thawing sample temperature annotated with observations. The observations are generated based on the data received from the thawing machine. For example, with reference to FIG. 14, the observation is "User loaded the vial". The observation "User loaded the vial" is determined from the received sensor data, for example, the time at which the thawing machine sensed that a vial had been added.

In addition, the operator of the thawing machine, user 320, 321, 322, . . . , 32*n*, may also create user observations and add notes, which are also transferred from the thawing machine to the remote server 130, as user data. For example, when a biological sample is being thawed as part of a clinical trial, the user 320, 321, 322, . . . , 32*n* may add observations, such as the time that the sample was administered to the patient, following thawing of the sample. These user observations are added at the thawing machine via the user interface and transferred to the remote server 130. According to another embodiment, user observations may be added via an application, to the remote server 130.

The received sensor data, thawing machine data, sample data and/or user data, which relates to the thawing of the sample in accordance with the predetermined thawing profile received at the remote server 130 can be analysed in order to perform checks on the thawing process. For example, a predetermined thawing profile may require approximately 500 joules of energy to complete the thaw. When five of the thawing machines transfer data indicating that they completed the predetermined thawing profile using approximately 500 joules of energy, but one of the thawing machines transfers data indicating that it completed the predetermined thawing profile using 800 joules of energy, then it is possible to determine that an unknown event has occurred at that thawing machine, and further investigation is required. Previously it would not have been possible to compare such data and therefore, it would not have been possible to identify that an unknown event has occurred at the thawing machine which required further investigation.

Figure 17:
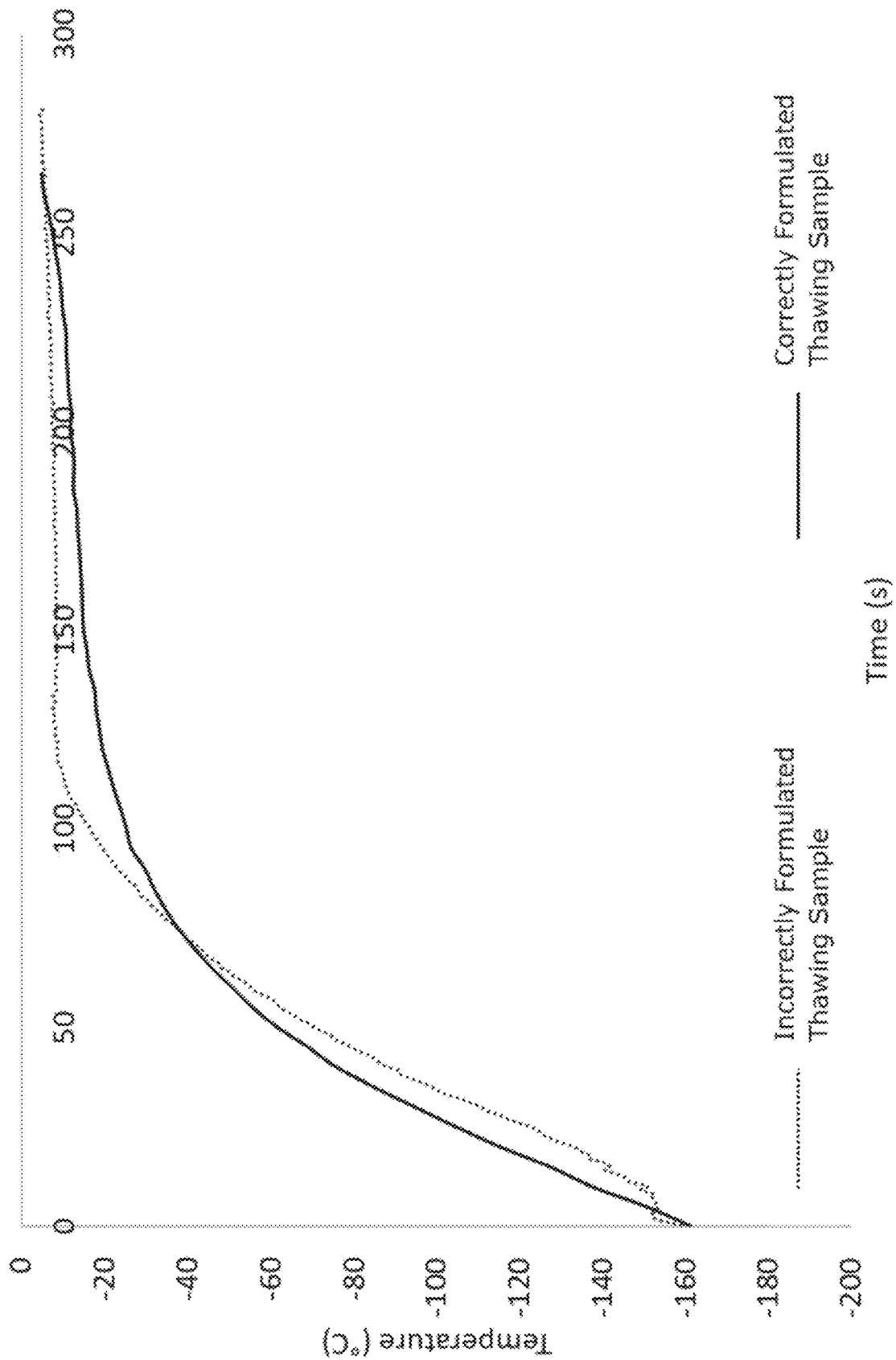
FIG. 17 illustrates a graph of two different sets of detected thawing temperatures.

FIG. 17 illustrates a graph of two different sets of detected thawing temperatures, both of which relate to the thawing of a sample in accordance with the same predetermined thawing profile. The two different sets of thawing temperatures were recorded by temperature sensors at a thawing machine and were received at the remote server 130. The solid line indicates the temperatures detected whilst thawing a sample having a 10% aqueous DMSO solution, and the dashed line indicates the temperatures detected whilst thawing a sample having an 'incorrectly' formulated solution, where the DMSO was not added. It would be apparent to any skilled person in the field when viewing the graph of FIG. 17, that due to the different warming rates—as well as the much higher temperature plateau which is indicative of the melting point of a solution—that the 'incorrectly' formulated solution deviated from a correct formulation. The ability to compare data from a plurality of different thawing machines and/or a plurality of different thaws is advantageous since incorrect thaws can be identified quickly, which can act as a quality control of the solutions. In addition, the data received at the server 130 can be referred to immediately after a thaw, and may also be referred back to at a later time, since the data is saved at the server.

According to one embodiment, the remote server may provide a suggestion as to what the cause of a deviation from a predetermined thawing profile and/or a deviation between data detected using the same predetermined thawing profile might be. For example, when the thawing temperature plateaus are different, then the remote server may indicate that the freezing solution has been incorrectly formulated.

According to one embodiment, the remote server may also be able to provide alerts to a user. For example, the thawing machine may comprise an alarm to indicate to a user in the proximity of the thawing machine that the added vial is too hot. However, the remote server may also be able to provide alerts direct to a user, such as to users mobile device, when an event has occurred at a thawing machine. The alerts may be visual and/or audible alerts.

Further quality control information and other information can be determined through differential thermal analysis (DTA) on the detected data which is transmitted to the remote server. DTA can be performed on the data received from freezers, thawing machines and transportation devices (described below). The following example refers to data received from a freezer. As described above, a freezer transmits detected sensors data (such as the detected temperature of the sample plate during the freezing cycle), and/or freezer data (such as the voltage supplied to the freezer during the freezing cycle) and/or sample data (such as the selected predetermined freezing profile) and/or user data etc. By, for example, integrating the detected power curves shown in FIG. 18, it is possible to calculate the energy required for the freezing cycle.

Figure 18:
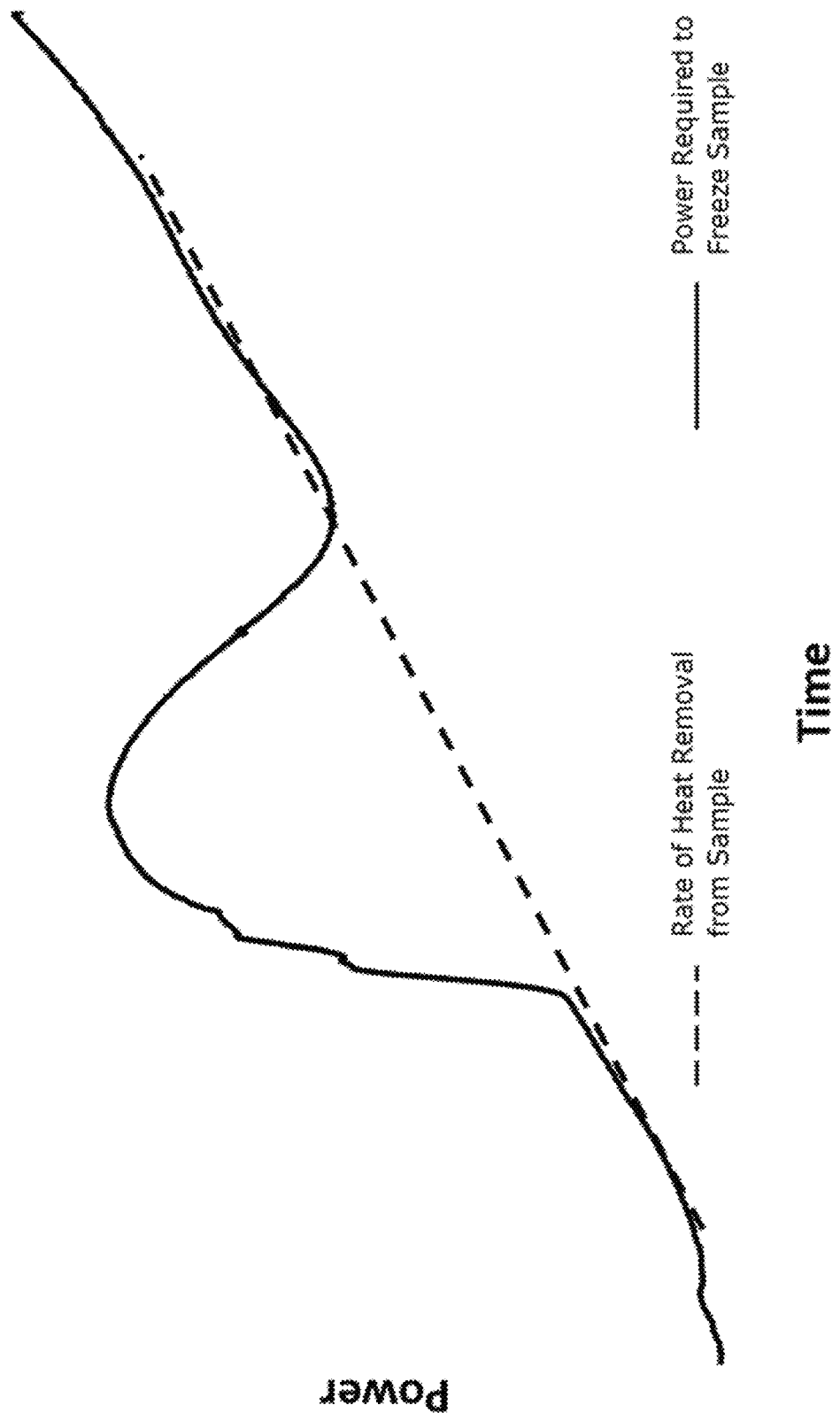
FIG. 18 illustrates a graph of the power required to cool a biological sample through the ice formation region.

From the measured power-time curve for the sample freezing example illustrated in FIG. 18, it is possible to relate the measured power consumed during the freezing cycle (the solid line) to the expected power removed from the sample during the freezing cycle (the dashed line). After nucleation and during the bulk of the phase change there is a large increase in power required to maintain the linear rate of temperature reduction (power is illustrated with a solid line in FIG. 18) which may be recorded and transmitted to the remote server. Before nucleation and also after the bulk of the freezing, FIG. 18 shows that the measured power is increasing approximately linearly with time—this is how the dashed expected power line is derived. However, it is known that before nucleation the rate of heat removal from a sample (with constant mass and specific heat capacity) must be constant when the temperature is being reduced linearly. This means that the approximately linear power, prior to nucleation must represent a constant "baseline" rate of heat removal from the sample (dashed line FIG. 18), together with an additional linearly increasing power requirement of the freezer to supply the plate itself and any losses in the system. This recorded power data profile before and after bulk ice formation (dashed line in FIG. 18) can readily be subtracted from the measured power being removed from the sample (solid line in FIG. 18), and obtain direct estimates of the changes in heat release during freezing.

To do this for this, for example, the regions between the curves in FIG. 18 can be integrated, using Simpson's rule or any other appropriate method clear to a skilled person, between nucleation, where the lines diverge, and the point where the lines re-join.

This data can be used to determine the total amount of ice formed, and if different from a predicted or separate control sample would indicate to the skilled person that for example, either volume or composition of the freeing sample was incorrect. In addition, the large increase in power which is recorded at the freezer and transmitted to the remote server indicates when ice nucleated during the freezing cycle and at what temperature.

Additionally, according to another example, the power recorded at a thawing machine and transmitted to the remote server during a thawing cycle may be used to determine the heat capacity of the solution, which can be compared with known values for quality control.

Returning to FIG. 9, following freezing, a sample may be required to be stored and/or transported to another location prior to thawing. To simplify tracking of each sample, each sample may be provided with a unique identifier (sample ID), such as a bar code, a QR code or an identification code, which may be any combination of numbers and/or letters. When a sample is frozen, it's sample ID may be input by a user 120, 121, 122, . . . , 12n at the freezer 100, 101, 102, . . . , 10n. For example, when the sample ID is a bar code, then the user may scan the bar code prior to freezing the sample using a bar code scanner. The sample ID is then associated with the predetermined freezing profile which is selected by the user 120, 121, 122, . . . , 12n, the detected sensor data, the freezer data, the sample data and/or the user data, which relates to the freezing of a sample in accordance with the predetermined freezing profile, as discussed above.

In addition, when a sample is to be thawed, it's sample ID may be input by a user 320, 321, 322, . . . , 32n at the thawing machine 300, 301, 302, . . . , 30n. For example, when the sample ID is a bar code, then the user may scan the bar code prior to thawing the sample using a bar code scanner. The sample ID is then associated with the predetermined thawing profile which is selected by the user 320, 321, 322, . . . , 32n, the detected sensor data, the thawing machine data, the sample data and/or the user data, which relates to the thawing of a sample in accordance with the predetermined thawing profile, as discussed above.

It is possible for a user 140 of the remote server to search for all entries associated with a specific sample ID. The user 140 is then able to track the sample, from freezing to thawing.

The remote server is capable of transmitting a predetermined transportation profile to a transportation device which transports (and stores) a sample following cryogenic freezing to a different location. As with a thawing profile, a transportation profile is normally simpler than a freezing profile and specifies, for example: a temperature at which the sample is to be stored; container type; container size (ml); a minimum and maximum humidity for the sample; a minimum and maximum g force for the sample; what temperature will trigger a "too warm" alert; what temperature will trigger a "too cold" alert; what time will trigger a "too long" alert when a sample has been stored for too long etc. According to one embodiment, a transportation profile is defined as a list of instructions.

A user at a transportation device is only required to select the appropriate predetermined transportation profile, from a plurality of predetermined transportation profiles, via the user interface 14, such as a touch screen, at the transportation device. The user at the transportation device may also be required to enter their user ID, via the user interface 14, before using the transportation device. The user at the transportation device may also be required to enter the sample ID, via the user interface 14, such as by using a bar code scanner etc., before using the transportation device.

Figure 15:
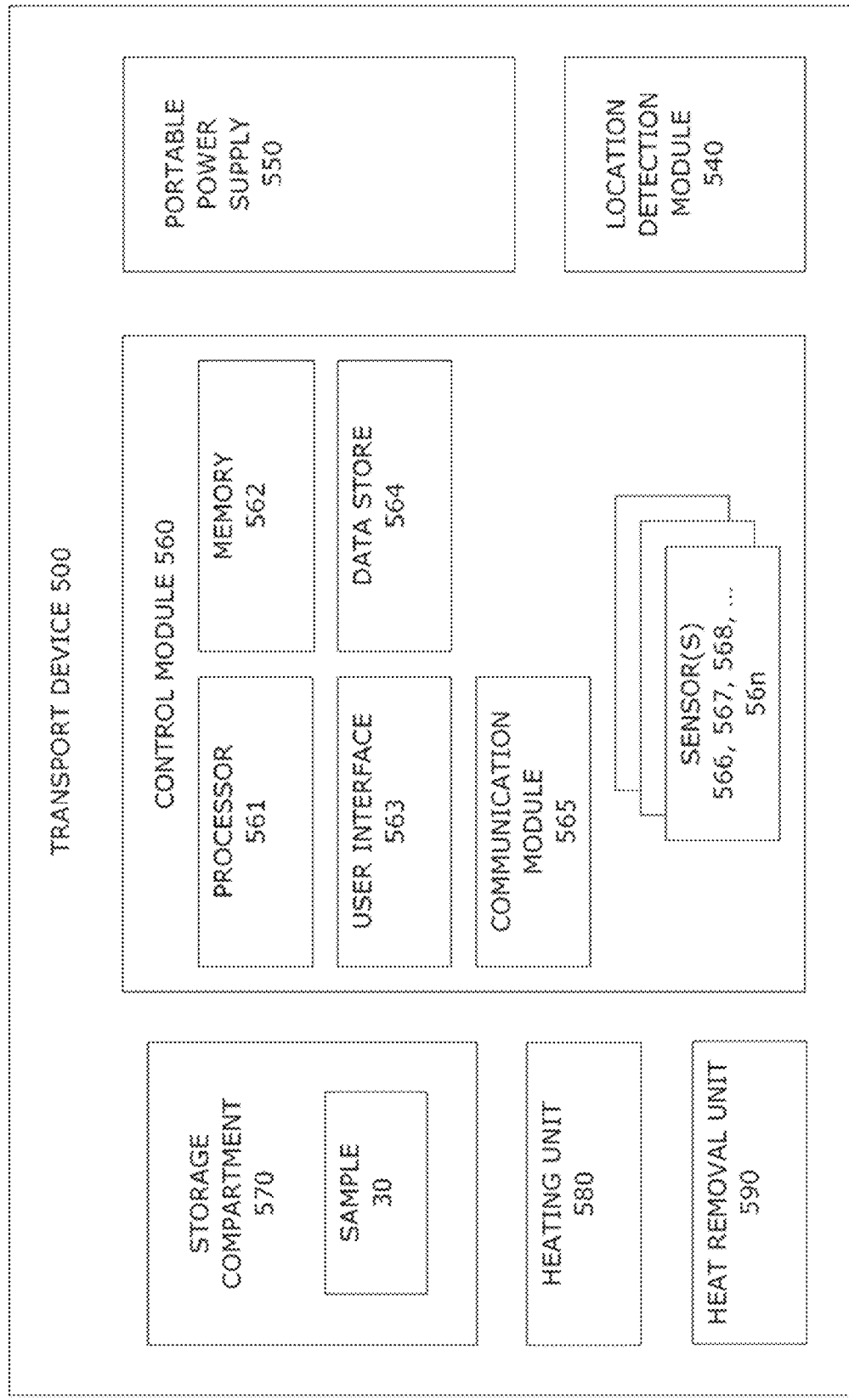
FIG. 15 schematically illustrates a storage device.

The remote server is also capable of receiving data from a transportation device which stores and transports a sample following cryogenic freezing. FIG. 15 schematically illustrates a cryogenic transportation device 500. A cryogenic transportation device 500 comprises a portable power supply 550, such as a battery, and/or may also be connected to a power supply provided in a transportation vehicle.

As can be seen from FIG. 15, a transportation device 500 comprises a storage compartment 570, within which a sample 30 is provided, coupled to a heating unit 580 and a heat removal unit 590. The storage device is required to keep the sample at a constant temperature. The transportation device 500 also comprises a control module 560 comprising at least one processor 561 coupled to at least one memory 563, at least one user interface 563, at least one communications interface 565, at least one data store 564, at least one sensor 566, 567, 568, . . . 56n, and at least one location detection module 540. The storage device 500 may also comprises other elements which are not illustrated.

The memory 563 may comprise program memory for storing computer program code to control the heating unit 580 and the heat removal unit 590 in order to maintain the sample 30 at a constant temperature in the storage compartment 570, and working memory for storing data, programs, or instructions received or processed by the processor 561. The memory 563 and/or the data store 564 may comprise a volatile memory such as random access memory (RAM), for use as temporary memory. Additionally or alternatively, the memory 563 and data store 564 may comprise non-volatile memory such as Flash, read only memory (ROM) or electrically erasable programmable ROM (EEPROM).

The processor 561 may comprise processing logic to process data (for example, data received from the sensors 566, 567, 568, . . . 56n, the location detection module 540, programs, instructions received from a user via the user interface 563 etc.) and generate output signals in response to the processing. The control module 560 may comprise any suitable circuitry or logic, and may, for example, comprise any one or more of the following: a field programmable gate array (FPGA), system on chip device, microprocessor device, microcontroller, and one or more integrated circuits. The control module 560 is coupled to the heating unit 580 and the heat removal unit 590 in order to control the temperature in the storage compartment 570.

The user interfaces 563 may be one or more of a computer screen, a touch screen, a keyboard, a mouse, speakers, a bar code scanner, a fingerprint scanner etc.

The communication module 565 may be conFigured to receive data or data signals from one or more external devices (such as a remote server as described herein). The communication module 565 may be a communication interface or unit. The communication module may be conFigured to receive data via a wired or wireless network, such as the internet. The communication module may also be conFigured to transmit data or data signals to one or more external devices (such as a remote server) via a wired or wireless network, such as the internet.

The data store 564 may be conFigured to store data from the sensors 566, 567, 568, . . . 56n and the location detection module 540. The data store 564 may be coupled to the at least one communication module 565 and the at least one processor 561.

The location detection module 540 may be any device capable of detecting the location of the transportation device 500, such as a GPS location device.

The components of the control module 560 may be a combination of hardware and software components, all software components, or all hardware components.

As stated above, the transportation device 500 comprises at least one sensor 566, 567, 568, . . . 56n. One, or more of the sensors 566, 567, 568, . . . 56n comprise temperature sensors provided to monitor the temperature within the storage compartment 570 during transportation. The detected temperatures are stored in the data store 564 together with a sensor ID and the time at which the temperature was sensed.

In addition to detecting the temperatures within the transportation device during storing, one or more sensors 566, 567, 568, . . . 56n may be provided to detect the external temperature at the transportation device 500. In addition, one or more sensors may be provided to detect when the door of the transportation device 500 is opened, when the door of the transportation device 500 is closed, the time and date at which the door is opened/closed, and/or the duration of time the door was open. In addition, one, or more of the sensors 566, 567, 568, . . . 56n may comprise g force sensors provided to detect the g force applied to the transportation device 500 during transportation. In addition, one, or more of the sensors 566, 567, 568, . . . 56n may comprise humidity sensors provided to detect internal and/or external humidity at the transportation device 500 during transportation. In addition, one or more of the sensors 566, 567, 568, . . . 56n may detect the orientation of the transportation device 500. In addition, one, or more of the sensors 566, 567, 568, . . . 56n may detect the power supply at the transportation device 500, for example, when the transportation device 500 is connected to a vehicles power supply, when the transportation device 500 requires power form the portable power supply 550, when the transportation device 500 is running out of power (for example when the portable power supply 550 has only 20% power left etc.).

According to one embodiment, the sensors 566, 567, 568, . . . 56n detect continuously during transportation. According to another embodiment, the sensors 566, 567, 568, . . . 56n detect periodically during transportation.

The sensor data detected by the sensors 566, 567, 568, . . . 56n relates to the transportation of a sample in accordance with the sample transportation profile data. The transportation sensor data detected by the sensors 566, 567, 568, . . . 56n may comprise one or more of: the temperature within the storage compartment; the external temperature at the transportation device; transportation device door data, such as when the door of the transportation device is opened and/or closed during storage; g force at the transportation device; orientation of the transportation device; internal and/or external humidity at the transportation device; power connection; battery life. For each detection, the time and date of the detection is also recorded together with an indication of the detecting sensor.

In addition to the sensor data detected by the sensors 566, 567, 568, . . . 56n, the control module 560 is also capable of detecting and storing other data which relates to the transportation of the sample. The other data may comprise transportation device data and/or sample data and/or user data etc. The control module 560 may store transportation device data such as: a transportation device identifier; transportation device energy consumption (such as the energy consumed by the transportation device during storage and/or by different components of the transportation device during storage); the location of transportation device (such as the actual location, for example GPS coordinates, of the transportation device); transportation device alarm data, such as whether an alarm was activated at the transportation device (for example, a sample too warm alarm, and whether any action was taken in response to the alarm); the power supply at the transportation device; the amount of power available at the transportation device (for example remaining battery power). The control module 360 may store sample data such as: a sample identifier; information regarding the composition of the sample; information regarding the size/weight of the sample; information regarding the sample container; the predetermined freezing profile; the predetermined transportation profile data; the predetermined thawing profile; the date the sample was frozen. The control module 560 may store user data such as: a user identifier; user observations.

The data detected by the sensors 566, 567, 568, . . . 56n, as well as the other data, all of which relates to the transportation of a sample may be transferred to a remote server 50, such as described above and illustrated in FIG. 6, via the communication module 565 at the transportation device.

Figure 16:
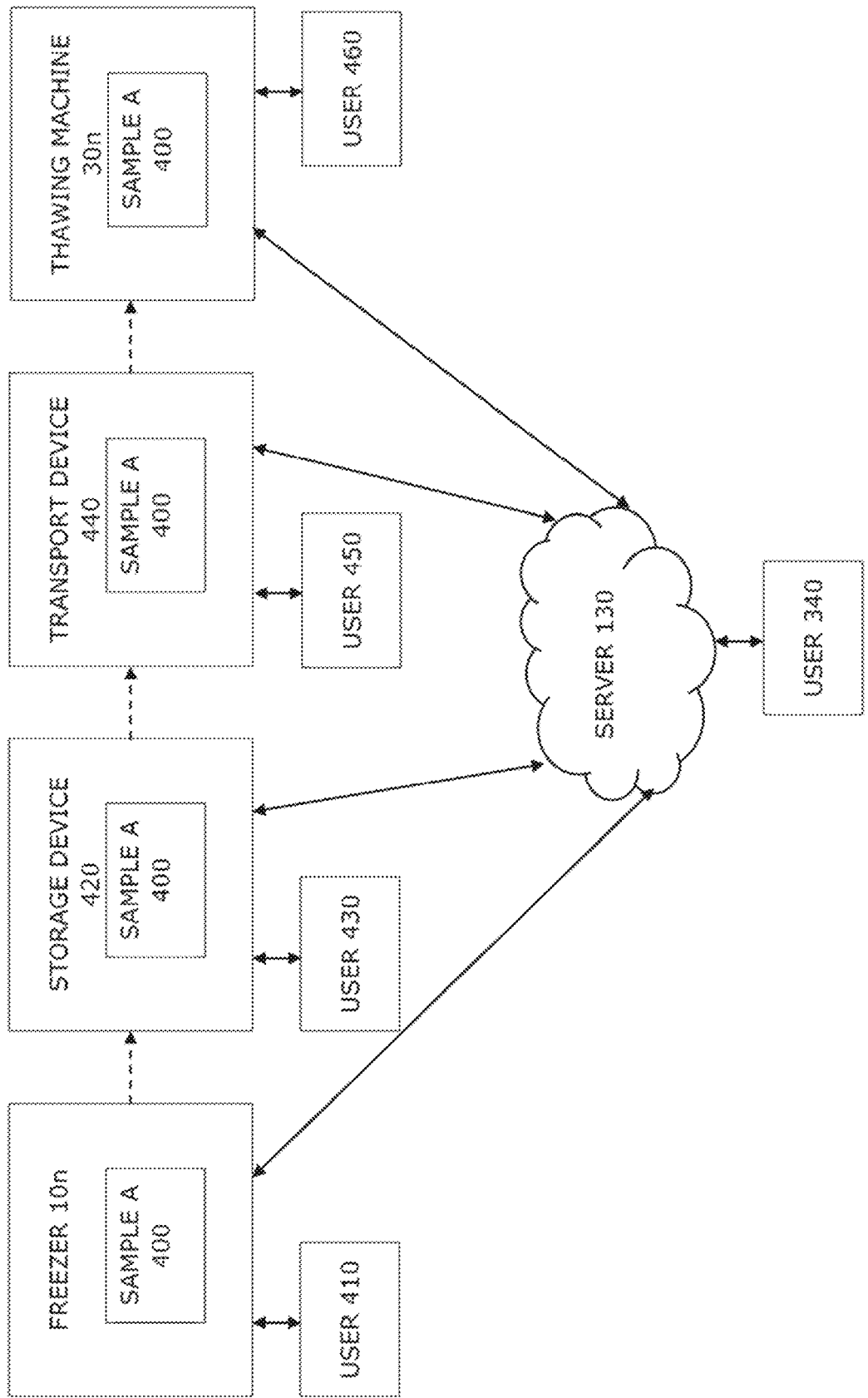
FIG. 16 schematically illustrates schematically a remote system for monitoring one or more devices for use in the cryogenic processing of a sample.

FIG. 16 illustrates schematically a remote system for monitoring one or more devices for use in the cryogenic processing of a sample. As illustrated in FIG. 16, the remote server 130 is conFigured to receive data from a freezer 10n regarding the freezing of a sample, to receive data from a storage device 420 regarding the storage of the sample, to receive data from a transportation device 440, when a sample is to be transported to a different location, regarding the storage/transportation of the sample, and to receive data from a thawing machine 30n regarding the thawing of a sample. The data recorded at each of these devices may be transferred to the remote server, either continuously, periodically or at the end of each stage in the process as required. Although only one freezer 10n, storage device 420, transportation device 440 and thawing machine 30n is illustrated in FIG. 16, the remote server 130 is capable of communicating with a plurality of freezers 10n, a plurality of storage devices 420, a plurality of transportation devices 440 and a plurality of thawing machine 30n.

The remote server 130 is communicatively coupled to at least one transportation device 440. According to one embodiment, the communication module 60 is used to connect the remote server to at least one transportation device 440 over a network, such as the Internet. The connection may be wired or wireless. The plurality of transportation devices are able to exchange data with the remote server 130. For example, the plurality of transportation devices are capable of transmitting data to the remote server 130, and the remote server 130 is capable of receiving the transmitted data from the plurality of transportation devices. In addition, the remote server 130 is capable of transmitting data to the plurality of transportation devices and the plurality of transportation devices are capable of receiving the transmitted data from the remote server 130.

According to one embodiment, the data which is transferred between the transportation device and the server is encrypted, for example, using a private/public key pair etc.

The transportation profiles are predetermined by skilled scientists. The predetermined transportation profiles are provided together with their associated criteria, such as the composition of the sample, the size of the sample, the amount of cryoprotectant DMSO to be added to the sample, the type of container in which the sample is to be provided etc. to the remote server 130. According to one embodiment, the remote server 130 transmits the predetermined transportation profiles to a plurality of transportation devices. The predetermined transportation profiles may be transmitted to the plurality of transportation devices at substantially the same time. When a predetermined transportation profile is updated by a skilled scientist, an updated version of the predetermined transportation profile can may be distributed to the plurality of transportation devices from the remote server. The updated predetermined transportation profiles may be transmitted to the plurality of transportation devices at substantially the same time.

When a sample is required to be transported, a user at the transportation device is only required to select the appropriate predetermined transportation profile, from a plurality of predetermined transportation profiles, via the user interface 563, such as a touch screen, at the transportation device. The user at the transportation device is not required to manually enter the predetermined transportation profile into the transportation device. The user at the transportation device may also be required to enter their user ID, via the user interface 563, before using the transportation device. The user at the transportation device may also be required to enter the sample ID, via the user interface 563, such as by using a touch screen, a bar code scanner when the sample ID is stored as a bar code, an imaging device when the sample ID is stored as a QR code etc., before using the transportation device.

As is understood in the art, an actual detected transportation data may vary from the predetermined transportation profile.

When a predetermined transportation profile is selected at a transportation device, and a sample is transported in accordance with the selected predetermined transportation profile, the detected sensor data, transportation device data, sample data and/or user data, which relates to the transportation of the sample in accordance with the predetermined transportation profile, is transmitted from the transportation device to the remote server 130. The data may be transferred from the transportation device to the remote server continuously or periodically, as required. Accordingly, the remote server may receive the data in near-real time. The remote server 130 stores the received data in the data store 56.

The detected transportation data, which relates to the transportation of a sample in accordance with the predetermined transportation profile, may be transferred from the transportation device to the remote server 130 as a graph. Alternatively, the detected transportation data, which relates to the transportation of a sample in accordance with the predetermined transportation profile, may be transferred from the transportation device to the remote server 130 as a plurality of data logs of what actually happened whilst the sample was being transportation. In another alternative, the detected transportation data, which relates to the transportation of a sample in accordance with the predetermined transportation profile, may be transferred from the transportation device to the remote server 130 as a combination of graph(s) and/or a plurality of data logs.

When the remote server 130 receives a plurality of data logs, the remote server may generate an actual transportation graph from the plurality of data logs, representing the transportation of the sample in the transportation device.

A user 140 can then access the received data, which relates to the transportation of a sample in accordance with the predetermined transportation profile, at the remote server 130. The server 130 can provide the user with the data from one or more transportation devices and/or transportations. The data regarding the plurality of transportations at the plurality of different transportation devices can then be presented to the user 140 in a user-friendly format.

The freezer/thawing machine/transportation device transmits the data to the remote server via the internet. According to one embodiment, the freezer/thawing machine/transportation device retains the data in its local data store until receipt of the data by the remote server is confirmed. This ensures that the data is not deleted until it has been safely stored at the remote server, for example in the data store 56. The freezer/thawing machine/transportation device may then delete the data if required. Whether the freezer/thawing machine/transportation device deletes the transmitted data will depend on the size of the data store provided at the freezer/thawing machine/transportation device. According to one embodiment, the data is stored at the freezer/thawing machine/transportation device for a predetermined period of time, such as one week, one month, one year etc. prior to deletion.

A user 140 is then able to review the data received by the remote server 130. The user 140 is also able to search the data based on criteria, such as the freezer ID, freezing profile, sample ID, thawing machine ID etc. For example, when examining a predetermined freezing profile, it may appear that a better result is achieved by one freezer and/or user; or that one freezer always produces freezing profiles that deviate from the predetermined profile by a greater amount than the other freezers. It is then possible for the user 140 to further investigate that freezer, for example, it may appear that the freezer is not functioning correctly. However, without being able to compare the freezer's results with other freezers, this malfunction would not be immediately apparent.

The ability to compile the data as well as filter and organise the data from a plurality of devices and samples, increases the usability of the data since further analysis can be performed which previously was not possible or not practical. The server can also be used to generate reports and/or graphs as required by the user 140 and discussed above.

Since the server 130 is connected to the internet, the user 140 of the server does not need to be at the server 130 in order to access the data. This is particularly useful when clinical trials are being carried out at several different locations. The data regarding each process (i.e. freezing/storing/transporting/thawing etc.) can be transferred in near real time to the user running the trial.

An example of a generated report, generated by the remote server, is a report which present the data from multiple freezes (using the same predetermined freezing profile), or multiple thaws (using the same predetermined thawing profile) in such a way as to make an anomaly obvious to the user. According to one embodiment, the data from multiple freezes, or multiple thaws are provided on the same time v's temperature graph such that an anomaly is clearly visible to the user.

The user 140 is able to select the group for which each report is to be generated. For example, the user may select: a plurality of freezer, selected using the freezer ID's; a plurality of thawing machines, selected using the thawing machine ID's; a plurality of freezes, selected using the predetermined freezing profile; a user ID's; a plurality of samples, selected using the sample ID's etc. It is also possible for the user 340 to select a group for which each report is to be generated based on the country in which the machines are based, selected using the location ID; or all the devices owned by a particular company, selected using the device ID (freezer ID, thawing machine ID, transportation device ID etc.); or all the devices taking part in a particular trial, selected using the device ID (freezer ID, thawing machine ID, transportation device ID etc.).

Furthermore, since the remote server provides the predetermined freezing profile, thawing profile and/or transportation profile to the freezers, thawing machines and/or transportation devices, it is possible to select a group of devices to receive each specific profile, and different devices may receive different profiles/version of profiles based on a user selected criteria. For example, all devices belonging to the same company may receive a first predetermined profile, whereas all devices belonging to a different company may receive a different predetermined profile.

It is further possible for a user to create rules which are then applied to an individual device, all the devices, or a subset of the devices as required by the user. An example, of such as rule predefined at the remote server, may be the thawing machine determines that the sample is too warm when it was loaded, from the temperature data, and the thawing machine generates a warning locally at the thawing machine, the rule might be that the remote server also generates a task for a user to review this log because it has an associated warning. Other examples of rules are: if a freeze or thaw log is missing information like details of the sample being processed, the remote server generates a task for a user to add this information; a summary of the previous week's equipment logs is emailed to a specified user weekly at a set time; if any thaws are aborted or fail at thawing machines A, B or C, email User Y immediately to warn them etc.

According to another embodiment, the remote server is also capable of transmitting instructions to the freezer/thawing machine/transportation device as required. For example, the remote server may send instructions to a freezer to begin cooling down in the early hours of the morning in order to prepare for use when an operator gets into work.

According to another embodiment, the remote server is also capable of generating and transmitting alerts, such as door open, temperature too hot/too cold etc. There may be an alarm which is active at the device. However, the server may also generate and transmit alerts to a user, for example via a user's mobile device. The user's response to the alert may also be recorded, such as user cancelled action, user over rid the alarm etc.

According to another embodiment, the remote server may also be used to prompt a user at the freezer/thawing machine to perform a task—for example, once a sample has defrosted, a user may be prompted by the remote server to remove the sample from the thawing machine. This may be in addition to alerts set at the freezer/thawing machine.

According to another embodiment, a user at the remote server may also interact with the remote server, for example, via a web page in order to add observations and/or annotate observations regarding the received thawing, freezing or transport data logs. For example, the user may add an observation to explain an anomaly once it has been investigated.

According to another embodiment, the remote server may generate invoices. For example, once a sample has been thawed for use, the remote server generates an invoice from the manufacture of the sample to the user of the sample.

As will be appreciated by one skilled in the art, the present techniques may be embodied as a system, method or computer program product. Accordingly, the present techniques may take the form of an entirely hardware embodiment, an entirely software embodiment, or an embodiment combining software and hardware.

Furthermore, the present techniques may take the form of a computer program product embodied in a computer readable medium having computer readable program code embodied thereon. The computer readable medium may be a computer readable signal medium or a computer readable storage medium. A computer readable medium may be, for example, but is not limited to, an electronic, magnetic, optical, electromagnetic, infrared, or semiconductor system, apparatus, or device, or any suitable combination of the foregoing.

Computer program code for carrying out operations of the present techniques may be written in any combination of one or more programming languages, including object oriented programming languages and conventional procedural programming languages.

For example, program code for carrying out operations of the present techniques may comprise source, object or executable code in a conventional programming language (interpreted or compiled) such as C, or assembly code, code for setting up or controlling an ASIC (Application Specific Integrated Circuit) or FPGA (Field Programmable Gate Array), or code for a hardware description language such as Verilog™ or VHDL (Very high speed integrated circuit Hardware Description Language).

Code components may be embodied as procedures, methods or the like, and may comprise sub-components which may take the form of instructions or sequences of instructions at any of the levels of abstraction, from the direct machine instructions of a native instruction set to high-level compiled or interpreted language constructs.

It will also be clear to one of skill in the art that all or part of a logical method according to the preferred embodiments of the present techniques may suitably be embodied in a logic apparatus comprising logic elements to perform the steps of the method, and that such logic elements may comprise components such as logic gates in, for example a programmable logic array or application-specific integrated circuit. Such a logic arrangement may further be embodied in enabling elements for temporarily or permanently establishing logic structures in such an array or circuit using, for example, a virtual hardware descriptor language, which may be stored and transmitted using fixed or transmittable carrier media.

In one alternative, an embodiment of the present techniques may be realized in the form of a computer implemented method of deploying a service comprising steps of deploying computer program code operable to, when deployed into a computer infrastructure or network and executed thereon, cause said computer system or network to perform all the steps of the method.

In a further alternative, the preferred embodiment of the present techniques may be realized in the form of a data carrier having functional data thereon, said functional data comprising functional computer data structures to, when loaded into a computer system or network and operated upon thereby, enable said computer system to perform all the steps of the method.

It will be clear to one skilled in the art that many improvements and modifications can be made to the foregoing exemplary embodiments without departing from the scope of the present techniques.

The invention claimed is:

1. A system for remotely monitoring cryogenic processing of a sample, the system comprising:
    at least one transportation device for transporting the sample;
    a remote server located remote from the transportation device, the remote server being configured to one or both of transmit or receive sample transportation profile data to or from the at least one transportation device;
    wherein the at least one transportation device comprises at least one sensor, the at least one sensor configured to detect transportation sensor data relating to the transportation of the sample in accordance with the sample transportation profile data;
    wherein the remote server is further configured to receive the detected transportation sensor data from the at least one transportation device; and
    wherein the remote server is further configured to one or both of transmit or receive the same predetermined sample transportation profile data to or from the at least one transportation device.

2. The system of claim 1, wherein the at least one transportation device further comprises a control module, the control module configured to detect at least one of transportation device data, sample transportation data and user data, relating to the transportation of the sample in accordance with the sample transportation profile data; and
    wherein the remote server is further configured to receive from the transportation device the detected transportation device data, sample transportation data and/or user data.

3. The system of claim 1, wherein the remote server is further configured to:
    transmit an update to the sample transportation profile data to the at least one transportation device; and
    receive the detected data continuously or periodically from the at least one transportation device.

4. The system of claim 1, wherein the remote server is further configured to, in response to deviation between the sample transportation profile and the detected data received from the at least one transportation device, provide a suggestion as to a cause of the deviation.

5. The system of claim 1, wherein the remote server is configured to one or both generate an actual transportation graph from the detected data received from the at least one transportation device or compare the sample transportation profile to the detected data received from the at least one transportation device.

6. The system of claim 3, further comprising a plurality of transportation devices, wherein the remote server is configured to one or more of:
    (i) compare actual transportation graphs generated for the plurality of transportation devices;
    (ii) compare the detected data received from the plurality of transportation devices; or
    (iii) compare the detected data received from a group of transportation devices selected from the plurality of transportation devices.

7. The system of claim 5, wherein the remote server is further configured to, in response to deviation between actual transportation graphs generated for the plurality of transportation devices, provide a suggestion as to a cause of the deviation.

8. The system of claim 6, wherein the remote server is further configured to, in response to deviation between detected data received from the plurality of transportation devices, provide a suggestion as to a cause of the deviation.

9. The system of claim 1, wherein the transportation sensor data comprise one or more of: at least one temperature within a storage compartment of the at least one transportation devices during transportation; an external temperature at the at least one transportation device; transportation device door data; g force at the at least one transportation device; orientation of the transportation device; internal humidity at the at least one transportation device; external humidity at the at least one transportation device, power connection data; or battery life data.

10. The system of claim 2, wherein the transportation device data comprises one or more of: a transportation device identifier; transportation device energy consumption data; transportation device location data; or transportation device alarm data.

11. The system of claim 2, wherein the sample transportation data comprises one or more of: a sample identifier; sample composition data; sample size data; sample container data; sample freezing profile data; sample transportation profile data; sample thawing profile data; or sample transportation date.

12. The system of claim 1, wherein the or each transportation device comprises, a user interface, the user interface configured to receive user inputs relating to the transportation of the sample in accordance with the sample transportation profile data; and wherein the remote server is further configured to receive the user inputs.

13. A method for remotely monitoring cryogenic processing of a sample, the method comprising:
    transmitting and receiving sample transportation profile data from a remote server to at least one transportation device;
    transporting the sample in the at the least one transportation device in accordance with the sample transportation profile data;
    detecting at the least one transportation device, transportation sensor data relating to the transportation of the sample in accordance with the sample transportation profile; and
    receiving at the remote server the detected transportation sensor data from the at least one transportation device.

14. The method of claim 13, further comprising:
    detecting at the at least one transportation device, at least one of transportation device data, sample transportation data and user data, relating to the transportation of the sample in accordance with the sample transportation profile data; and
    receiving at the remote server the detected transportation device data, sample transportation data and/or user data from the at least one transportation device.

15. The method of claim 13, further comprising:
    transmitting an update to the sample transportation profile data from the remote server to the at least one transportation device.

16. The method of claim 13, further comprising one or more of:
    receiving at the remote server the detected data continuously or periodically from the at least one transportation device;

generating at the remote server an actual transportation graph from the detected data received from the at least one transportation device; or comparing at the remote server the sample transportation profile data to the detected data received from the at least one transportation device.

17. The method of claim 16, wherein the at least one transportation device comprises a plurality of transportation devices; and the method further comprises one or more of:

comparing at the remote server the actual transportation graphs generated for the plurality of transportation devices;

comparing at the remote server the detected data received from the plurality of transportation devices; or comparing at the remote server the detected data received from a group of transportation devices selected from the plurality of transportation devices.

18. The method of claim 13, wherein the transportation sensor data comprise one or more of: at least one temperature within a storage compartment of the at least one transportation devices during transportation; an external temperature at the at least one transportation device; transportation device door data; g force at the at least one transportation device; orientation of the transportation device; internal and/or external humidity at the at least one transportation device; power connection data; or battery life data.

19. The method of claim 14, wherein the transportation device data comprises one or more of: a transportation device identifier; transportation device energy consumption data; transportation device location data; or transportation device alarm data.

20. A cryogenic transportation device for transporting a cryogenically frozen sample in accordance with a sample transportation profile data, the transportation device comprising:

a communication module configured to receive the sample transportation profile data from a remote server;

at least one sensor configured to detect transportation sensor data relating to the transportation of the sample in accordance with the sample transportation profile data; and wherein the communication module is further configured to transmit the detected transportation sensor data to the remote server; and wherein the remote server is further configured to one or both of transmit or receive the same predetermined sample transportation profile data to or from the at least one transportation device.

21. The transportation device of claim 20, further comprising:

a control module configured to detect at least one of transportation device data, sample transportation data and user data, relating to the transportation of the sample in accordance with the sample transportation profile data; and wherein the communication module is further configured to transmit the detected transportation device data, sample transportation data and/or user data to the remote server.

22. The transportation device of claim 20, wherein the communication module is further configured to receive an update to the sample transportation profile data from the remote server.

23. The transportation device of claim 20, wherein the communication module is further configured to transmit the detected data continuously or periodically to the remote server.

24. The transportation device of claim 20, wherein the transportation sensor data comprise one or more of: at least one temperature within a transportation compartment of the at least one transportation device during transportation; an external temperature at the at least one transportation device; transportation device door data; g force at the at least one transportation device; orientation of the at least one transportation device; internal and/or external humidity at the at least one transportation device; power connection data; or battery life data.

25. The transportation device of claim 20, wherein the transportation device data comprises one or more of: a transportation device identifier; transportation device energy consumption data; transportation device location data; or transportation device alarm data.

26. The transportation device of claim 20, wherein the sample transportation data comprises one or more of: a sample identifier; sample composition data; sample size data; sample container data; sample freezing profile data; sample transportation profile data; sample thawing profile data; or sample transportation date.

27. The transportation device of claim 20, further comprising:

a user interface configured to receive user inputs relating to transportation of the sample in accordance with the sample transportation profile data, wherein the communication module is further configured to transmit the user inputs to the remote server;

a data store configured to store the detected data prior to transmitting the detected data to the remote server; and a portable power supply.

28. A system for remotely monitoring cryogenic processing of a sample, the system comprising:

at least one transportation device for transporting the sample;

a remote server located remote from the transportation device, the remote server being configured to one or both of transmit or receive sample transportation profile data to or from the at least one transportation device;

wherein the at least one transportation device comprises at least one sensor, the at least one sensor configured to detect transportation sensor data relating to the transportation of the sample in accordance with the sample transportation profile data;

wherein the remote server is further configured to receive the detected transportation sensor data from the at least one transportation device; and wherein the remote server is configured to one or both generate an actual transportation graph from the detected data received from the at least one transportation device or compare the sample transportation profile to the detected data received from the at least one transportation device.

* * * * *